(12) United States Patent
Khandaker et al.

(10) Patent No.: US 10,932,910 B2
(45) Date of Patent: Mar. 2, 2021

(54) NANOFIBER COATING TO IMPROVE BIOLOGICAL AND MECHANICAL PERFORMANCE OF JOINT PROSTHESIS

(71) Applicant: UNIVERSITY OF CENTRAL OKLAHOMA, Edmond, OK (US)

(72) Inventors: Morshed Khandaker, Edmond, OK (US); Shahram Riahinezhad, Fort Lee, NJ (US); William Paul Snow, Edmond, OK (US)

(73) Assignee: University of Central Oklahoma, Edmond, OK (US)

( * ) Notice: Subject to any disclaimer, the term of this patent is extended or adjusted under 35 U.S.C. 154(b) by 44 days.

(21) Appl. No.: 16/248,122

(22) Filed: Jan. 15, 2019

(65) Prior Publication Data
US 2019/0142593 A1 May 16, 2019

Related U.S. Application Data

(63) Continuation-in-part of application No. 15/791,571, filed on Oct. 24, 2017, now Pat. No. 10,206,780, (Continued)

(51) Int. Cl.
*A61F 2/28* (2006.01)
*A61F 2/30* (2006.01)
(Continued)

(52) U.S. Cl.
CPC ............ *A61F 2/28* (2013.01); *A61F 2/30771* (2013.01); *A61F 2/36* (2013.01); *A61F 2/38* (2013.01);
(Continued)

(58) Field of Classification Search
CPC ...... A61F 2/28; A61F 2/36; A61F 2/38; A61F 2002/30771; A61F 2002/2817;
(Continued)

(56) References Cited

U.S. PATENT DOCUMENTS 692,631 A 2/1902 Cooley
1,975,504 A 10/1934 Formhals
(Continued)

FOREIGN PATENT DOCUMENTS

CN 1687493 A 10/2005
CN 1766181 A 5/2006
(Continued)

OTHER PUBLICATIONS

Carnell, Lisa A., et al., "Aligned Mats from Electrospun Singer Fibers", Macromolecules, vol. 41, No. 14, Jun. 26, 2008, pp. 5345-5349.
(Continued)

*Primary Examiner* — Alvin J Stewart
(74) *Attorney, Agent, or Firm* — Berenato & White, LLC

(57) ABSTRACT

The present invention provides a process to functionalize nanofiber membrane (NFM) on a total joint replacement (TJR) implant surface to support bone ingrowth and reduce macrophage-associated inflammation, the process comprising amending the implant surface by laser cutting microgrooves greater than 100 μm in depth to protect functional PCL NFM from applied loading, induce a higher amount of osteoblast cell function, increase implant-bone contact area, and serve as a reservoir for the local delivery of biomolecules to increase osseointegration of the implant; depositing aligned fibers on the implant surface, the fibers aligned in the direction of the microgrooves and collected in layers until a thickness less than 30 μm is reached and preferably in the range of 1 μm to 10 μm. Biofunctionalized NFM are used to indirectly attach biomolecules on said implant surface, or extracellular matrix proteins with biomolecules are immobilized and deposited on the PCL NFM coated implant.

20 Claims, 33 Drawing Sheets

Related U.S. Application Data which is a continuation of application No. 15/467,652, filed on Mar. 23, 2017, now Pat. No. 9,809,906, which is a continuation-in-part of application No. 14/734,147, filed on Jun. 9, 2015, now Pat. No. 10,415,156, application No. 16/248,122, which is a continuation-in-part of application No. 15/976,615, filed on May 10, 2018, now Pat. No. 10,286,103, which is a continuation of application No. 15/674,309, filed on Aug. 10, 2017, now Pat. No. 9,974,883.

(60) Provisional application No. 62/312,041, filed on Mar. 23, 2016, provisional application No. 62/038,506, filed on Aug. 18, 2014, provisional application No. 62/373,786, filed on Aug. 11, 2016.

(51) Int. Cl.
| | |
|---|---|
| *D01D 5/00* | (2006.01) |
| *D01F 6/62* | (2006.01) |
| *A61F 2/36* | (2006.01) |
| *A61F 2/38* | (2006.01) |
| *D01F 1/10* | (2006.01) |

(52) U.S. Cl.
CPC ......... *D01D 5/0007* (2013.01); *D01D 5/0084* (2013.01); *D01F 6/625* (2013.01); *A61F 2002/2817* (2013.01); *A61F 2002/3082* (2013.01); *A61F 2002/3084* (2013.01); *A61F 2002/30677* (2013.01); *A61F 2002/30838* (2013.01); *A61F 2002/30909* (2013.01); *A61F 2310/00023* (2013.01); *D01F 1/10* (2013.01); *D10B 2331/041* (2013.01); *D10B 2509/00* (2013.01)

(58) Field of Classification Search
CPC .... A61F 2002/30677; A61F 2002/3082; A61F 2002/30838; A61F 2002/3084; D01D 5/0007; D01D 5/0084
See application file for complete search history.

(56) References Cited

U.S. PATENT DOCUMENTS

| | | | |
|---|---|---|---|
| 2,109,333 A | 2/1938 | Formhals | |
| 2,123,992 A | 7/1938 | Formhals | |
| 2,187,306 A | 1/1940 | Formhals | |
| 2,349,950 A | 5/1944 | Formhals | |
| 4,536,894 A | 8/1985 | Galante et al. | |
| 4,636,219 A | 1/1987 | Pratt et al. | |
| 4,655,769 A | 4/1987 | Zachariades | |
| 5,013,324 A | 5/1991 | Zolman et al. | |
| 5,370,698 A | 12/1994 | Heimke et al. | |
| 5,507,833 A | 4/1996 | Bohn | |
| 5,672,284 A | 9/1997 | Devanathan et al. | |
| 6,106,913 A | 8/2000 | Scardino et al. | |
| 6,312,473 B1 | 11/2001 | Oshida | |
| 6,355,699 B1 | 3/2002 | Vyakarnam et al. | |
| 6,743,273 B2 | 6/2004 | Chung et al. | |
| 6,753,454 B1 | 6/2004 | Smith et al. | |
| 6,821,479 B1 | 11/2004 | Smith et al. | |
| 7,575,707 B2 | 8/2009 | Xia | |
| 7,828,539 B1 | 11/2010 | Beachley et al. | |
| 7,879,093 B2 | 2/2011 | Wei et al. | |
| 8,097,274 B2 | 1/2012 | Coombes et al. | |
| 8,157,554 B2 | 4/2012 | Petras et al. | |
| 8,475,531 B1 | 7/2013 | Maxson et al. | |
| 8,691,542 B2 | 4/2014 | Guilak et al. | |
| 8,728,170 B1 | 5/2014 | Atanasoska et al. | |
| 9,095,524 B2 | 8/2015 | Warnke et al. | |
| 9,180,223 B2 | 11/2015 | Yu et al. | |
| 9,327,448 B2 | 5/2016 | Shah et al. | |
| 9,359,694 B2 | 6/2016 | Khandaker et al. | |
| 9,428,849 B2 | 8/2016 | Haynie et al. | |
| 9,618,501 B2 | 4/2017 | Mohapatra et al. | |
| 9,649,409 B2 | 5/2017 | Guilak et al. | |
| 9,737,632 B2 | 8/2017 | Johnson et al. | |
| 9,809,906 B2 * | 11/2017 | Khandaker | D01F 1/10 |
| 10,206,780 B2 * | 2/2019 | Khandaker | D01F 1/10 |
| 10,286,103 B2 * | 5/2019 | Khandaker | A61L 24/0094 |
| 2002/0104606 A1 | 8/2002 | Ohzuru et al. | |
| 2005/0137675 A1 | 6/2005 | Dubson et al. | |
| 2005/0142163 A1 | 6/2005 | Hunter et al. | |
| 2005/0224998 A1 | 10/2005 | Andrady et al. | |
| 2005/0276841 A1 | 12/2005 | Davis et al. | |
| 2006/0226580 A1 | 10/2006 | Xia et al. | |
| 2007/0269481 A1 | 11/2007 | Li | |
| 2007/0275458 A1 | 11/2007 | Gouma | |
| 2008/0112998 A1 | 5/2008 | Wang | |
| 2008/0170982 A1 | 7/2008 | Zhang et al. | |
| 2008/0290554 A1 | 11/2008 | Wu et al. | |
| 2009/0108503 A1 | 4/2009 | Scott-Carnell et al. | |
| 2009/0118813 A1 | 5/2009 | Scheuermann et al. | |
| 2009/0196901 A1 | 8/2009 | Guilak et al. | |
| 2009/0226600 A1 | 9/2009 | Dang et al. | |
| 2009/0294733 A1 | 12/2009 | Branham et al. | |
| 2009/0317446 A1 * | 12/2009 | Tan | A61L 27/3821 424/423 |
| 2009/0324680 A1 | 12/2009 | Reneker et al. | |
| 2009/0324950 A1 | 12/2009 | Kim | |
| 2010/0009267 A1 | 1/2010 | Chase et al. | |
| 2010/0028387 A1 | 2/2010 | Balasundaram et al. | |
| 2010/0028999 A1 | 2/2010 | Nain | |
| 2010/0113857 A1 | 5/2010 | Ramakrishna et al. | |
| 2010/0119578 A1 | 5/2010 | To et al. | |
| 2010/0168771 A1 | 7/2010 | Guldberg et al. | |
| 2010/0197027 A1 | 8/2010 | Zhang et al. | |
| 2010/0310623 A1 | 12/2010 | Laurencin et al. | |
| 2010/0327494 A1 | 12/2010 | Jabbari | |
| 2010/0331980 A1 | 12/2010 | Lee et al. | |
| 2011/0066242 A1 | 3/2011 | Lu et al. | |
| 2013/0030452 A1 | 1/2013 | Itskovitz-Eldor et al. | |
| 2013/0110138 A1 | 5/2013 | Hurtado et al. | |
| 2013/0115457 A1 | 5/2013 | Haynie et al. | |
| 2013/0138155 A1 * | 5/2013 | Hoornaert | A61B 17/8085 606/283 |
| 2013/0273801 A1 | 10/2013 | Young | |
| 2014/0079759 A1 | 3/2014 | Patel et al. | |
| 2014/0205971 A1 | 7/2014 | Wang | |
| 2014/0271786 A1 | 9/2014 | Bagga et al. | |
| 2014/0271795 A1 | 9/2014 | Phaneuf et al. | |
| 2015/0024025 A1 * | 1/2015 | Floyd | A61L 27/56 424/425 |
| 2015/0165092 A1 | 6/2015 | Kaplan et al. | |
| 2015/0273110 A1 | 10/2015 | McClellan et al. | |
| 2015/0283298 A1 | 10/2015 | Kaplan et al. | |
| 2015/0290354 A1 | 10/2015 | Loboa et al. | |
| 2016/0047063 A1 | 2/2016 | Khandaker et al. | |
| 2016/0047064 A1 | 2/2016 | Khandaker et al. | |
| 2016/0106886 A1 | 4/2016 | Dvir et al. | |
| 2016/0228611 A1 | 8/2016 | Castro et al. | |
| 2016/0250393 A1 | 9/2016 | Jeong et al. | |
| 2016/0367722 A1 * | 12/2016 | Bumgardner | A61L 15/28 |
| 2016/0374820 A1 | 12/2016 | Khandaker et al. | |
| 2017/0072089 A1 | 3/2017 | Nseir Manassa et al. | |
| 2017/0100912 A1 | 4/2017 | Tricoli et al. | |
| 2017/0130194 A1 | 5/2017 | Lee et al. | |
| 2017/0143874 A1 | 5/2017 | Vickers | |
| 2017/0167064 A1 | 6/2017 | Taylor et al. | |
| 2018/0057963 A1 | 3/2018 | Khandaker et al. | |
| 2018/0161185 A1 | 6/2018 | Kresslein et al. | |
| 2018/0193209 A1 * | 7/2018 | Rajamani | D01F 1/10 |
| 2018/0221146 A1 | 8/2018 | Jana et al. | |
| 2018/0221537 A1 | 8/2018 | Johnson et al. | |
| 2018/0230626 A1 | 8/2018 | Knothe Tate | |
| 2019/0262105 A1 * | 8/2019 | Tapaltsyan | A61K 6/891 |
| 2020/0197153 A1 * | 6/2020 | MacEwan | A61L 15/42 |

FOREIGN PATENT DOCUMENTS

| | | |
|---|---|---|
| CN | 1776033 A | 5/2006 |
| CN | 103893828 A | 7/2014 |

(56) References Cited

FOREIGN PATENT DOCUMENTS

| CN | 104906637 A | 9/2015 |
|---|---|---|
| EP | 2045375 A1 | 4/2009 |
| WO | WO2004074559 A1 | 9/2004 |
| WO | WO2005073442 A1 | 8/2005 |
| WO | WO2005123995 A1 | 12/2005 |
| WO | WO2006052039 A1 | 5/2006 |
| WO | WO2006135147 A1 | 12/2006 |
| WO | WO2009101472 A2 | 8/2009 |

OTHER PUBLICATIONS

Jianfeng Zhange, et al., "Preparation of biaxial orientation mats from single fibers," Advances in Polymer Technol. Wiley and Sons, Hoboken NJ, vol. 21, Jan. 1, 2018, pp. 606-608.

Partial EP search report for corresponding EP15833663 dated Apr. 12, 2018.

Yee, W.A., et al., "Stress-induced structural changes in electrospun polyvinylidene difluoride nanofibers collected using a modified rotating disk," Polymer, Elsevier Science Publishers, VG, GB vol. 49, No. 19, Sep. 2008, pp. 4196-4203.

Zussman E., et al.,"Assembly of electrospun nanofibers into crossbars," Nanotechnology, 2002, IEEE-NANO 2002, Proceedings of the 2002 2nd IEEE Conference on Aug. 26-28, 2002, Piscataway, NJ, Aug. 26, 2002, pp. 283-286.

Yarin et al., "Branching in electrospinning of nanofibers", Journal of Applied Physics 98, pp. 064501, 2005, pp. 1-12.

Ali et al., "Electrospinning of Continuous Nanofiber Bundles and Twisted Nanofiber Yarns", Nanofibers—Production, Properties and Functional Applications, 2011, pp. 153-174.

Bashar Haseeb, "Controlled deposition and alignment of electrospun PMMA-g-PDMS nanofibers by novel electrospinning setups", Master of Science Thesis, KTH Chemical Science and Engineering, Stockholm, Sweden 2011, 164 pages.

KdScientific, "Inflowmation Chronicles Highlights of Interesting Scientific Applications", Inflowmation Chronicles, Issue 1001, Spring 2009, 2 pages.

Li et al., "Electrospinning of Nanofibers: Reinventing the Wheel?**", Advanced Materials, 2004, vol. 16, No. 14, pp. 1151-1170.

Monika Rajput, "Optimization of Electrospinning Parameters to Fabricate Aligned Nanofibers for Neural Tissue Engineering", A Thesis Submitted in Partial Fulfillment of the Requirement for the Degree of Master of Technology in Biotechnology & Medical Engineering, Department of Biotechnology and Medical Engineering, National Institute of Technology, Rourkela, Orissa, India, 2012, 74 pages.

Neves et al., "Patterning of polymer nanofiber meshes by electrospinning for biomedical applications", International Journal of Nanomedicine, 2007, 2(3), pp. 433-448.

Peterson, "Hybrid Nanomanufacturing Process for High-Rate Polymer Nanofiber Production", University of Nebraska—Lincoln, DigitalCommons@University of Nebraska—Lincoln, Engineering Mechanics Dissertations & Theses, 2010, 159 pages.

Tan et al., "Tensile testing of a single ultrafine polymeric fiber", Biomaterials 26, 2005, pp. 1453-1456.

Theron et al., "Electrostatic field-assisted alignment of electrospun nanofibres", Nanotechnology, 12, 2001, pp. 384-390.

Khandaker, M.; Vaughan, M.; Coles, A.; Jamadagni, H.; Wolf, R.; Williams, W. Application of polycaprolactone nanofibers and mgo nanoparticles for a cemented implant surgery. In Proceedings of the 2017 Orthopaedic Research Society (ORS) Annual Meeting, San Diego, CA, USA, Mar. 19-22, 2017.

Po-Yee Lui, P.; Zhang, P.; Chan, K.-M.; Qin, L. Biology and augmentation of tendon-bone insertion repair. J. Orthop. Res. Surg. Res. 2010, 5.

Apedo, K.L.; Munzer, C.; He, H.; Montgomery, P.; Serres, N.; Fond, C.; Feugeas, F. Cement paste surface roughness analysis using coherence scanning interferometry and confocal microscopy. Mater. Charact. 2015, 100, 108-119.

Sultanova, Z.; Kaleli, G.; Kabay, G.; Mutlu, M. Controlled release of a hydrophilic drug from coaxially electrospun polycaprolactone nanofibers. Int. J. Pharm. 2016, 505, 133-138.

Wang H.B.; Mullins, M.E.; Cregg, J.M.; Hurtado, A.; Oudega, M.; Trombley, M.T.; Gilbert, R.J. Creation of highly aligned electrospun poly-l-lactic acid fibers for nerve regeneration applications. J. Neural Eng. 2009, 6, 016001.

Deravi, L.F.; Sinatra, N.R.; Chantre, C.O.; Nesmith, A.P.; Yuan, H.; Deravi, S.K.; Goss, J.A.; MacQueen, L.A.; Badrossamy, M.R.; Gonzalez, G.M.; et al. Design and fabrication of fibrous nanomaterials using pull spinning. Macromol. Mater. Eng. 2017, 302.

Chandaker, M.; Vaughan, M.; Morris, T.; White, J.; Meng, Z. Effect of additives particles on mechanical, thermal and cell functions properties of poly (methyl methacrylate) cement. Int. J. Nanomed. 2014, 9, 2699-2712.

Graham, J.; Ries, M.; Pruitt, L. Effect of bone porosity on the mechanical integrity of the bone-cement interface. J. Bone Jt. Surg. Am. vol. 2003, 85A, 1901-1908.

Kwon, I.K.; Kidoaki, S.; Matsuda, T. Electrospun nano- to microfiber fabrics made of biodegradable copolyesters: Structural characteristics, mechanical properties and cell adhesion potential. Biomaterials 2005, 26, 3929-3939.

Kumbar, S.G.; James, R.; Nukavarapu, S.P.; Laurencin, C.T. Electrospun nanofiber scaffolds: Engineering soft tissues. Biomed. Mater. 2008, 3.

Kim, G.H. Electrospun pcl nanofibers with anisotropic mechanical properties as a biomedical scaffold. Biomed. Mater. 2008, 3.

Chong, L.H.; Hassan, M.I.; Sultana, N. Electrospun polycaprolactone (pcl) and pcl/nano-hydroxyapatite (pcl/nha)-based nanofibers for bone tissue engineering application. In Proceedings of the 10th Asian Control Conference (ASCC), Kota Kinabalu, Malaysia, MaI 31 Jun. 3, 2015; pp. 1-4.

Moursi, A.M.; Winnard, A.V.; Winnard, P.L.; Lannutti, J.J.; Seghi, R.R. Enhanced osteoblast response to a polymethylmethacrylate-hydroxyapatite composite. Biomaterials 2002, 23, 133-144.

Mahalingam, S.; Edirisinghe, M. Forming of polymer nanofibers by a pressurised gyration process. Macromol. Rapid Commun. 2013, 34, 1134-1139.

Hickey et al., "Adding MgO Nanoparticles to Hydroxyapatite-PLLA Nanocomposites for Improved Bone Tissue Engineering Applications.", Acta Biomaterialia Dec. 2014, https://doi.org/10.1016/j.actbio.2014.12.004.

Saha, S.; Pal, S. Improvement of mechanical properties of acrylic bone cement by fiber reinforcement. J. Biomech. 1984, 17, 467-478.

Kanungo, I.; Fathima, N.N.; Rao, J.R.; Nair, B.U. Influence of pcl on the material properties of collagen based biocomposites and in vitro evaluation of drug release. Mater. Sci. Eng. C Mater. Biol. Appl. 2013, 33, 4651-4659.

Ries, M.D.; Rauscher, L.A.; Hoskins, S.; Lott, D.; Richman, J.A.; Lynch, F. Intramedullary pressure and pulmonary function during total knee arthroplasty. Clin. Orthop. Relat. Res. 1998, 356, 154-160.

Invitrogen. Click-it® Edu Imaging Kits. Available online: https://tools.thermofisher.com/content/sfs/manuals/mp10338.pdf (accessed on Oct. 26, 2017).

Liu et al Surface modification of titanium, titaniaum alloys, and related materials for biomedical applications., Materials Science and Engineering R 47 (2004), 73 pages.

Zupancic, S.; Baumgartner, S.; Lavric, Z.; Petelin, M.; Kristl, J. Local delivery of resveratrol using polycaprolactone nanofibers for treatment of periodontal disease. J. Drug Deliv. Sci.Technol. 2015, 30 Pt B, 408-416.

Wu, X.; Mahalingam, S.; VanOosten, S.K.; Wisdom, C.; Tamerler, C.; Edirisinghe, M. New generation of tunable bioactive shape memory mats integrated with genetically engineered proteins. Macromol. Biosci. 2017, 17.

Moffat, K.L.; Wang, I.N.; Rodeo, S.A.; Lu, H.H. Orthopedic interface tissue engineering for the biological fixation of soft tissue grafts. Clin. Sports Med. 2009, 28, 157-176.

Travan, A.; Marsich, E.; Donati, I.; Foulc, M.-P.; Moritz, N.; Aro, H.T.; Paoletti, S. Polysaccharide-coated thermosets for orthopedic applications: From material characterization to in vivo tests. Biomacromolecules 2012, 13, 1564-1572.

(56) References Cited

OTHER PUBLICATIONS

Lim, J.Y.; Shaughnessy, M.C.; Zhou, Z.; Noh, H.; Vogler, E.A.; Donahue, H.J. Surface energy effects on osteoblast spatial growth and mineralization. Biomaterials 2008, 29, 1776-1784.

Im, B.J.; Lee, S.W.; Oh, N.; Lee, M.H.; Kang, J.H.; Leesungbok, R; Lee, S.C.; Ahn, S.J.; Park, J.S. Texture direction of combined microgrooves and submicroscale topographies of titanium substrata influence adhesion, proliferation, and differentiation in human primary cells. Arch. Oral Biol. 2012, 57, 898-905.

Ferraz, E.P.; Sa, J.C.; De Oliveira, P.T.; Alves, C., Jr.; Beloti, M.M.; Rosa, A.L. The effect of plasma-nitrided titanium surfaces on osteoblastic cell adhesion, proliferation, and differentiation. J. Biomed. Mater. Res. Part A 2014, 102, 991-998.

Zankovych, S.; Diefenbeck, M.; Bossert, J.; Mückley, T.; Schrader, C.; Schmidt, J.; Schubert, H.; Bischoff, S.; Faucon, M.; Finger, U.; et al. The effect of polyelectrolyte multilayer coated titanium alloy surfaces on implant anchorage in rats. Acta Biomater. 2013, 9, 4926-4934.

Biggs, M.; Dalby, M.; Wilkinson, C.; Gadegaard, N.; Richards, G. The influence of nanoscale biomimetic structures on osteoblast adhesion. Comp. Biochem. Physiol. Part A Mol. Integr. Physiol. 2007, 146, S64.

Wagner, H.D.; Cohn, D. Use of high-performance polyethylene fibres as a reinforcing phase in poly(methylmethacrylate) bone cement. Biomaterials 1989, 10, 139-141.

Wenying Liu, Electrospun Nanofibers for Regenerative Medicine, 2012, Adv Healthc Mater, pp. 1-28.

Xie et al. Silver Nanoparticles and Growth Factors Incorporated Hydroxyapatite Coatings on Metallic Implant Surfaces for Enhancement of Osteoinductivity and Antibacterial Properties, ACS Appl. Mater. Interfaces, 2014, 2 pages.

\* cited by examiner

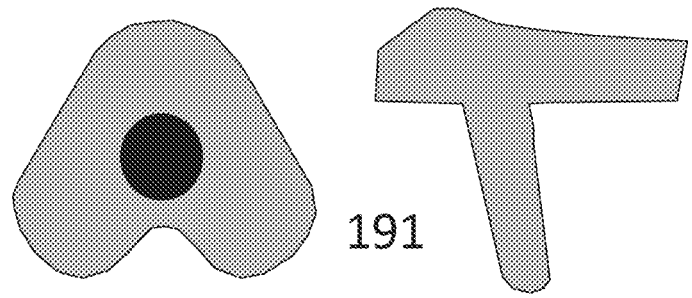
FIG. 19A
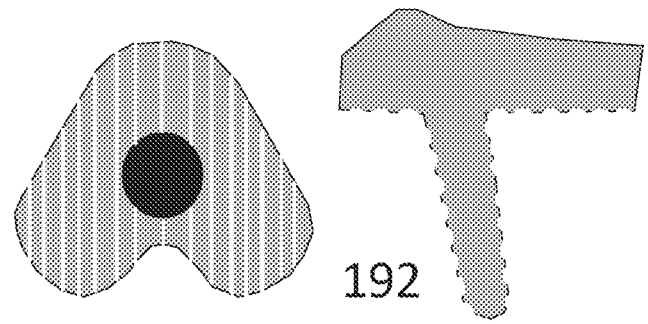
FIG. 19B
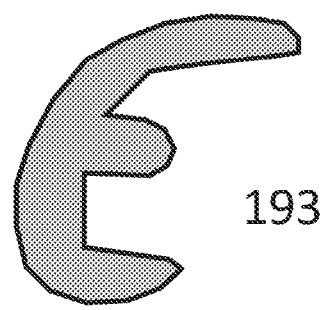
FIG. 19C
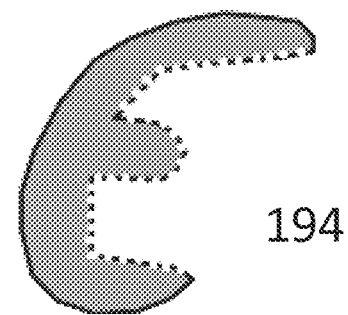
FIG. 19D
FIG. 19

NANOFIBER COATING TO IMPROVE BIOLOGICAL AND MECHANICAL PERFORMANCE OF JOINT PROSTHESIS

CROSS REFERENCES TO RELATED APPLICATIONS

This application is a continuation-in-part of U.S. patent application Ser. No. 15/791,571 filed Oct. 24, 2017 by the University of Central Oklahoma (Applicant), entitled "Method and apparatus to coat a metal implant with electrospun nanofiber matrix" the entire disclosure of which is incorporated herein by reference in its entirety for all purposes; which application is a continuation of U.S. patent application Ser. No. 15/467,652 filed Mar. 23, 2017 by the University of Central Oklahoma (Applicant) and now U.S. Pat. No. 9,809,906 issued Nov. 7, 2017, entitled "Method and apparatus to coat a metal implant with electrospun nanofiber matrix" the entire disclosure of which is incorporated herein by reference in its entirety for all purposes; which application claims the benefit of U.S. Provisional Patent Application No. 62/312,041 filed on Mar. 23, 2016 in the name of Morshed Khandaker and Shahram Riahinezhad, which is expressly incorporated herein by reference in its entirety and which application is also a continuation-in-part of U.S. patent application Ser. No. 14/734,147 filed Jun. 9, 2015 by the University of Central Oklahoma (Applicant), entitled "Method and apparatus for controlled alignment and deposition of branched electrospun fiber" the entire disclosure of which is incorporated herein by reference in its entirety for all purposes and which application claims the benefit of U.S. Provisional Patent Application No. 62/038,506 filed on Aug. 18, 2014 in the name of Morshed Khandaker and William Paul Snow, which is expressly incorporated herein by reference in its entirety.

This application is also a continuation-in-part of U.S. patent application Ser. No. 15/976,615 filed May 10, 2018 by the University of Central Oklahoma (Applicant), entitled "Method and apparatus to control the heterogeneous flow of bone cement and improve osseointegration of cemented implant"; which application is a continuation of U.S. patent application Ser. No. 15/674,309 filed Aug. 10, 2017 by the University of Central Oklahoma (Applicant) and now U.S. Pat. No. 9,974,883 issued May 22, 2018, entitled "Method and apparatus to control the heterogeneous flow of bone cement and improve osseointegration of cemented implant"; which application claims the benefit of U.S. Provisional Patent Application No. 62/373,786 filed on Aug. 11, 2016 in the name of Morshed Khandaker and Shahram Riahinezhad, which is expressly incorporated herein by reference in its entirety.

STATEMENT AS TO RIGHTS TO INVENTIONS MADE UNDER FEDERALLY SPONSORED RESEARCH OR DEVELOPMENT

This invention was made with government support under Grant Number 8P20GM103447 awarded by the National Institutes of Health. The government has certain rights in the invention.

FIELD OF THE INVENTION

The present invention generally relates to the field of polymer fiber production in relation to the field of prosthetics. More specifically, the invention relates to the attachment of fibers exhibiting micron to nano size diameters on different shapes of metallic implants from the nanofiber matrix produced in an electrospin process.

BACKGROUND OF THE INVENTION

Polycaprolecton (PCL) Electrospun Nanofibers (ENF) have numerous biomedical applications. Co-pending application Ser. No. 14/734,147 and U.S. Pat. No. 9,359,694 by the present Applicant disclose a method and apparatus for controlled deposition of branched ENF on biomedical implants and material. ENF have been found to be excellent carriers of drugs for improving the bone growth around a bio-medical implant. If applied as a coating around the implant, improved bone growth may reduce the implant loosening problem widely experienced with presently available implants. However, the use of PCL ENF matrix as a coating material for an implant has heretofore been severely limited because ENF fiber has poor adhesion with an implant surface, preventing use at physiological load bearing conditions.

An ideal implant for total joint arthroplasty or other types of implants, such as implants used in dental surgeries, has not yet been developed. When an implant is inadequate for osseointegration, micro-motions occur at the implant surface leading to activation of osteoclasts' resorption of bone around the implant, contributing to further implant loosening and eventual implant failure. Delayed bone healing has been reported in approximately 600,000 fractures per year in the United States. Along with the physical pain and suffering, implant loosening due to poor osseointegration and healing leads to economic burdens with the direct medical costs exceeding $3 billion alone annually.

Total joint (e.g., hip or knee) replacement surgeries are one of the greatest medical advances of modern medicine. Hip and knee replacements numbers are reaching 500,000 annually in the United States. Unfortunately, approximately ten percent of these replacements will fail resulting in complex revision surgeries, which are demanding on the patient and surgeon alike. A common cause of implant failure in total joint replacement (TJR) surgeries involves loosening at the bone-implant interface. This initiates with microfracture at the interface and progresses with cyclical structural loading most notably due to shear stresses. The rate of revision surgeries is expected to increase by 137% for total hip replacements and 601% for total knee replacements over the next 25 years as the population ages. Therefore, improving implant bone osseointegration is both clinically and economically important.

Degenerative bone diseases like arthritis and osteoporosis are prevalent in the growing geriatric population. Arthritic conditions such as rheumatoid arthritis and the high occurrences of bone fractures among the geriatric population drive the need for new and improved methods of treating those conditions. The Agency for Healthcare Research and Quality reports that about 53,000 people in the U.S. have shoulder replacement surgery each year, compared to more than 900,000 Americans a year who have knee and hip replacement surgery. By 2030, total knee replacement (TKR) surgeries are projected to grow 673% to 3.5 million procedures per year. PMMA-based cements have been widely used in TKR surgeries as implant fixation materials because of their strong mechanical, chemical, and biological properties. Although considerable advances have already been made, aseptic loosening of cemented components in TKR have been reported. A significant amount of resources and effort have been expended to reduce the likelihood of revision surgical intervention for TKR. An ideal cementing material for TKR surgeries should have adequate mechanical interlock and osseointegration to ensure the success of TKR surgeries. Since bone cement is a bio-inert material, the joining of cement with bone occurs by mechanical interlock. Currently, efforts to improve osseointegration are limited to the direct attachment of osteoinductive nanoscale materials with cement such as nanoparticles and nanowires. The main concern related to coating nanoscale materials onto a cement surface is the risk of coating detachment and the toxicity of related debris.

Bone loss leading to aseptic loosening of the prosthesis and periprosthetic fracture is the poor osseointegration of the implant surface. The life expectancy of TJR is contingent upon improving osseointegration between implant and bone. Revision TJR is associated with 3 to 8-fold greater in-hospital mortality, poorer functional outcome, longer hospital stay, and higher cost than primary surgery. There is a significant need to develop a method to improve osseointegration of a TJR implant. A method is needed to attach the ENF fibers to an implant surface for both regular and irregular shape implants. This method will also need to enable drug delivery and promote bone growth.

SUMMARY OF THE INVENTION

The process of the present invention provides methods to achieve adhesion of functional nanofiber coatings on a biomedical implant surface to increase the osteoinductive properties, and thereby to improve osseointegration of implant. The effects of fibers on the mechanical stability and osseointegration of an implant with and without fibers have not previously been known. In one aspect, a specific objective of the present invention is to provide methods to attach ENF fibers to an implant surface. Another objective of the present invention is to increase osseointegration at the tissue-cement interface by improving the bioactivity of cement using biocompatibility nanofiber membrane (NFM). Yet another objective of the present invention is to provide the means to apply nanofiber membrane (NFM) coating on implant surfaces for total cementless hip and knee replacement surgeries to improve the implant osseointegration. The methods provided by the present invention can be used for both regular and irregular shape implants, including implants used in shoulder replacement surgery.

The process of the present invention provides a method for coating a metal (e.g., titanium) implant with a functional coating made with PCL ENF and includes a set of steps by which PCL ENF can be bonded with the metal implant. The methods of the present invention can be implemented with the controlled electrospinning methods and apparatus disclosed herein, as well as in co-pending application Ser. No. 14/734,147 by the present Applicant, which methods are incorporated herein by reference in the entirety. The method of the present invention can also be implemented with other methods and processes for producing and applying micro to nano scale fibers to substrates, which methods are anticipated.

Previously reported approaches to improve osseointegration pursued direct attachment of osteoinductive nanoscale topographies on the implant surfaces. The main concern related to coating nanoscale materials onto an implant surface is the risk of coating detachment and toxicity of related debris. The present invention implements at least a set of grooves/ridges that are created on titanium (Ti) at the circumferential direction to increase the surface area of implant in contact with bone. These grooves/ridges protect the nanofiber matrix (NFM) made with Polycaprolactone (PCL) electrospun nanofiber (ENF) and collagen (CG) at the groove from physiological loading.

The present invention provides controlled fabrication of a microgrooves made with machine sawing, laser indentation, and titanium nitride (TiN) ion deposition around the circumference of Ti using a plasma nitride deposition technique. PCL ENF may be deposited along the sub-micrometer grooves with the help of plasma oxidation and collagen on Ti implant using a set of steps disclosed in this application. This method has proven through experimentation to be successful in increasing the in vivo mechanical stability and promoting osseointegration on Ti implants. The automatic production of micron to nano size grooves by laser indentation and TiN deposition as provided by the invention optimizes the groove topography on Ti. An extensive search of the related art revealed no reported research directed to the coating of Ti implant by NFM in relation to the influence of machine sawing, laser and TiN topography on the mechanical and biological performances of Ti.

The disclosures of U.S. patent application Ser. No. 15/674,309 filed Aug. 10, 2017 by the University of Central Oklahoma (Applicant) and now U.S. Pat. No. 9,997,883 issued May 22, 2018 recite a method for applying PCL ENF-CG coating on titanium including at least the following unique features:

1. The combined tailoring of interdigitation sites on Ti implant through microgrooving incorporated surface roughness to the implant and deposition of electrospun nanofiber matrix (NFM) on the grooving sites.

2. The use of a machine sawing technique is uniquely used to create controlled microgrooves on the circumference on Ti.

3. The use of nitrogen plasma, applied in semiconductor industry for nanoscale surface modification, is uniquely used to create TiN ridges on flat and circumference sides of a Ti rod.

4. The effects of the fiber diameter in PCL-CG NFM at the groove of Ti on the Ti-bone interaction may be enhanced to provide better bonding.

5. The effects of the attachment of osteoconductive nanoparticles (MgO) with PCL-CG nanofiber matrix at the groove of Ti on the Ti-bone interaction may be enhanced to provide better bonding.

6. At the groove, other biological glue such as PMMA cement, fibronectin, 2-octyl cyanoacrylate may be used to attach the PCL ENF.

In another aspect, microgrooves are fabricated on an implant by controlled formation of titanium nitride (TiN) ridges and the microgrooves are coated by CG-PCL NFM to produce higher biomechanical advantages compared to non-coated Ti implants due to increased biological compatibility of NFM coated Ti.

In another aspect, fibronectin (FN) and magnesium oxide nanoparticles (MgO NPs) immobilized PCL NFM coating are coupled with tresyl chloride-activated Ti implant to produce higher biomedical advantages compared to CG-PCL NFM due to the increased osteoinductive nature of the coatings.

In another aspect, CG-PCL NFM coating is used to act as resource for bone growth molecules (TGF-$\beta$, rhBMP) and antimicrobial agents (MgO, ZnO, Ag) to the adjoining bone tissue to have better osseointegration with the implant surface.

In another aspect, a process is provided to functionalize NFM on a total joint replacement (TJR) implant surface to support bone ingrowth and reduce macrophage-associated inflammation.

In another aspect, microgrooves greater than 100 μm depth are fabricated on implant surfaces by laser cutting to protect the functional PCL NFM from applied loading and induce a higher amount of osteoblast cell function and implant-bone contact area and serve as a reservoir for the local delivery of biomolecules to increase the osseointegration of implant.

In another aspect, the implant surface is chemically activated for direct immobilization of biomolecules (e.g. hydroxyapatite, extracellular matrix proteins or cytokines or enzymes).

In another aspect, a chemical activation method such as tresyl chloride method can be used to covalently bond proteins on implant surface.

In another aspect, a plasma ion deposition technique can be used to directly attached biomolecules on an implant surface.

In another aspect, biofunctionalized NFM are used to indirectly attach biomolecules on an implant surface.

In another aspect, aligned fibers are deposited on an implant surface amended with microgrooves, the fibers aligned in the direction of the microgrooves and collected until a thickness not exceeding 10 μm is achieved.

In another aspect, extracellular matrix proteins with biomolecules are immobilized and deposited on PCL NFM coated implant, with attachment of extracellular matrix proteins (eg. Collagen, fibronectin) with biomolecules [such as BMP2 (Bone Morphogenetic Protein 2) or PDGF (Platelet Derived Growth Factor), nanoparticles (Ag, MgO, $TiO_2$, ZnO), enzymes, (e.g. glutathione redox components), hormones (e.g insulin)] and complexes [such as fibronectin-BMP2 complex, fibronectin-heparin-PDGF complex].

BRIEF DESCRIPTION OF THE DRAWINGS

FIG. 19 shows non-limiting schematic representations of the application of a laser microgrooving on tibial and femoral trays in a TKR surgery: (A) Bottom and side views of the tibia tray without microgrooves, (B) Bottom and side views of the tibia tray with laser microgrooves, (C) cross-section view of the femoral tray without microgrooves, and (D) cross-section view of the femoral tray with laser microgrooves.

DETAILED DESCRIPTION OF PREFERRED EMBODIMENTS OF THE INVENTION

Figure 1:
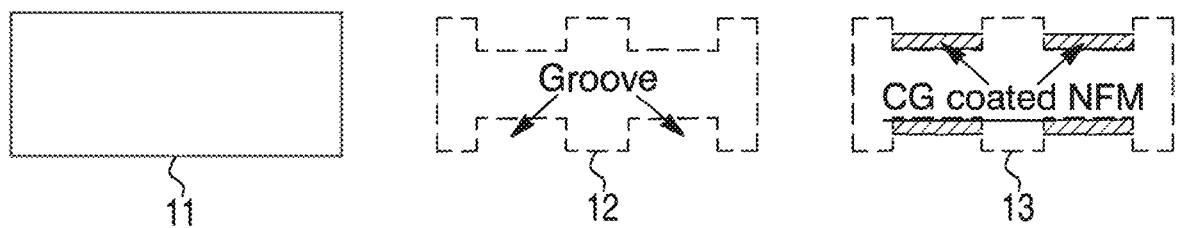
FIG. 1 is a non-limiting diagram showing the schematic images of longitudinal cross-section of a Ti rod without grooves, with circumferential grooves, and with circumferential grooves and nanofiber matrix (NFM) applied.

Referring now to FIG. 1, a non-limiting diagram shows schematic images of a longitudinal cross-section of a Ti rod without grooves 11, with circumferential grooves 12, and with circumferential grooves and nanofiber matrix (NFM) applied 13. The process of the present invention provides a method for controlled fabrication of microgrooves 12 around the circumference of a Ti implant 11. The present invention provides techniques to attach ENF fibers to an implant surface as shown positioned within the groves 13.

Figure 2:
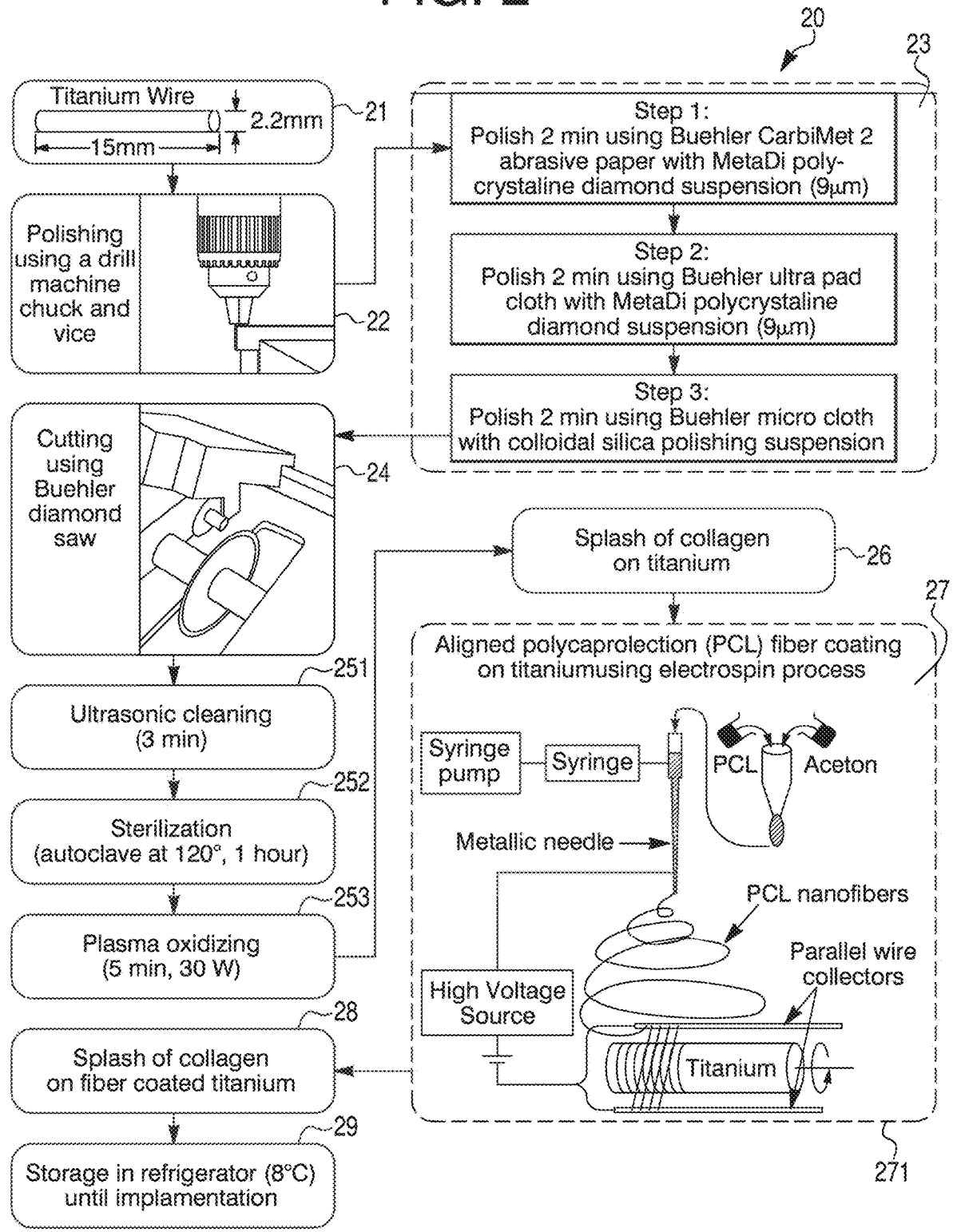
FIG. 2 is a non-limiting diagram showing a schematic representation of the process of the present invention for creating of microgrooves on Ti using machine sawing and depositing PCL-CG ENF on a Ti implant.
Figure 8:
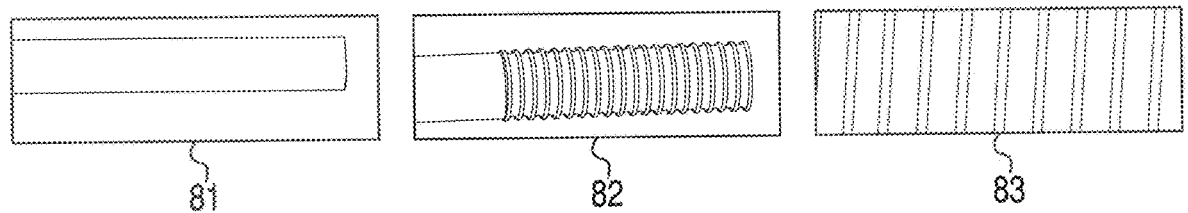
FIG. 8 is a non-limiting diagram showing a sample Ti rod fabricated without grooves 81, with grooves 82, and with grooves and nanofiber matrix (NFM) 83 applied using the methods of the present invention.

Referring now to FIG. 2, a non-limiting diagram shows the process of the present invention providing a method 20 for coating a metal implant with electrospun nanofiber, and includes a set of steps (shown in block diagram) by which PCL ENF can be bonded with the metal implant [See FIG. 8, 83]. Briefly, a Ti implant 21 (e.g., 2.2 mm×15 mm wire) may be polished using a drill machine chuck and gripper 22. Other functionally equivalent rotating devices may be used. A Ti implant may be secured at a drill chuck or by clamps on another type rotating device, and a polish paper (10 mm×50 mm) wrapped around the Ti implant with pressure using the gripper of the drill machine 22. Polishing can occur when the drill machine 22 or other rotating device is in operation. Ti wires samples have been circumferentially polished up to 8 mm from one end using this method. Similar results can be achieved for other cylindrical implants. The three steps polishing technique 23, as recommended by Buehler, Ltd., Evanston, Ill., can be used to polish the Ti implant. Other polishing techniques are possible. A diamond saw blade (Buehler Isomet wafer blade, 0.15 mm thickness, 15HC available from Buehler, Ltd., Evanston, Ill.) may be used to machine the microgroove on the circumferential surface of the implant (e.g., wire) 24. Ti implant (e.g., wire) can be fastened to the shaft of an electric motor or other type rotating machine 24. The motor can be secured in the saw machine 24 at the implant grip holder. Each microgroove can be created by running the motor and saw machine simultaneously in opposite directions for 8 seconds. In one preferred embodiment of the present invention, eighteen bands of circumferential parallel grooves are created starting at a 0.5 mm distance from one end of the Ti wire. The microgrooves are fabricated 0.05 mm apart from each other. The implant (e.g., wire) is then cleaned 251 in an ultrasonic cleaner followed by 70% ethanol wash 252 and autoclaved at 121° C. The Ti implant (e.g., wire) having grooves is exposed 253 to plasma $O_2$ for 5 minutes in a Zepto low pressure reactive ion etching system (Frequency: 40 kHz, power 30 watt) to increase the attachment of collagen to the Ti surface. The Ti implant (e.g., wire) is soaked 26 with a collagen solution and PCL electrospun nanofiber is deposited 27 on the Ti surface. Aligned PCL nanofibers are deposited on the grooved Ti implant using an electrospin setup 27. In one preferred embodiment, aligned PCL fibers can be collected between two parallel collectors 271 (e.g., wires or opposing plates). In another preferred embodiment, the method of the present invention can be implemented with the controlled electrospinning methods and apparatus disclosed in co-pending application Ser. No. 14/734,147. Collagen solution can be prepared by mixing 2.3 microliters of type I collagen with 0.23 microliters of acetic acid (0.02 M) and 195 microliters of deionized water in a vortex mixer. The Ti implant (e.g., wire) may be soaked 26 with the collagen solution. Aligned PCL ENF can be deposited on the Ti surface by rotating the Ti implant at least 6 times and dried in UV chamber. Rotation of the Ti implant can be accomplished either manually or using the methods disclosed in co-pending application Ser. No. 14/734,147. Finally, CG solution coating on Ti implant can be applied again 28 and dried to prepare the groove-NFM Ti surface. The groove-NFM implant can be kept at 4 degrees C. until implantation in the recipient. The topography of fibers can be examined on a carbon tape using Hitachi™ 3000 scanning electron microscope. The carbon tape can be wrapped around a Ti rod and the fibers collected on the tape by manually rotating the rod in a manner similar to the way fibers are collected on Ti for implants.

Figure 3:
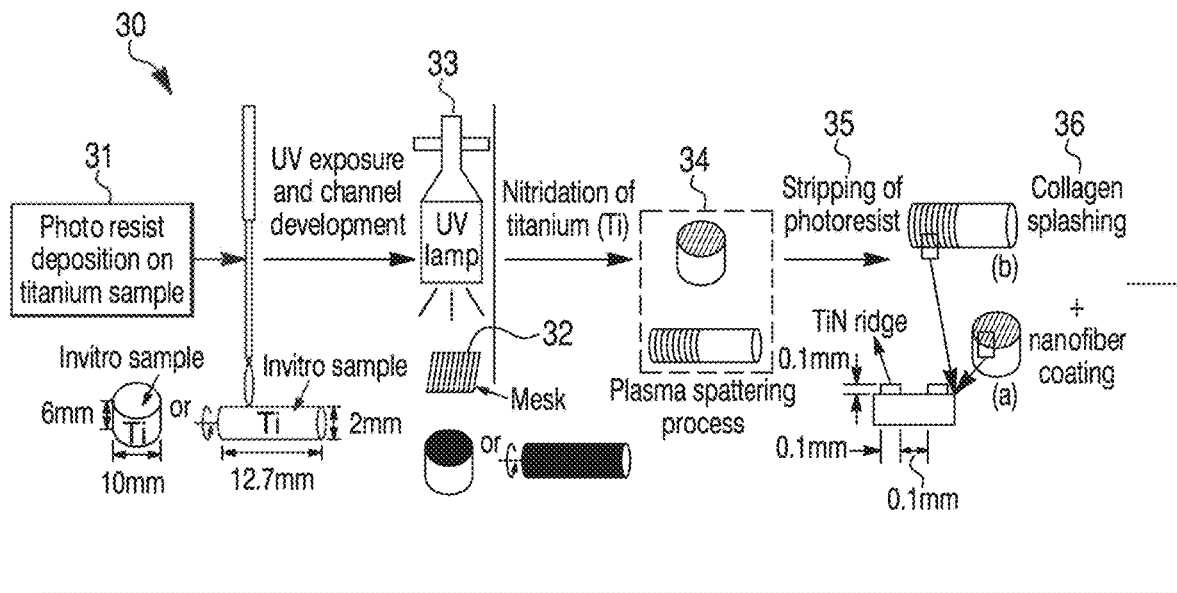
FIG. 3 is a non-limiting diagram showing a schematic representation of the method of the present invention providing controlled fabrication of ridge made with titanium nitride (TiN) around the circumference of a Ti substrate using a plasma nitride deposition technique.
Figure 3:
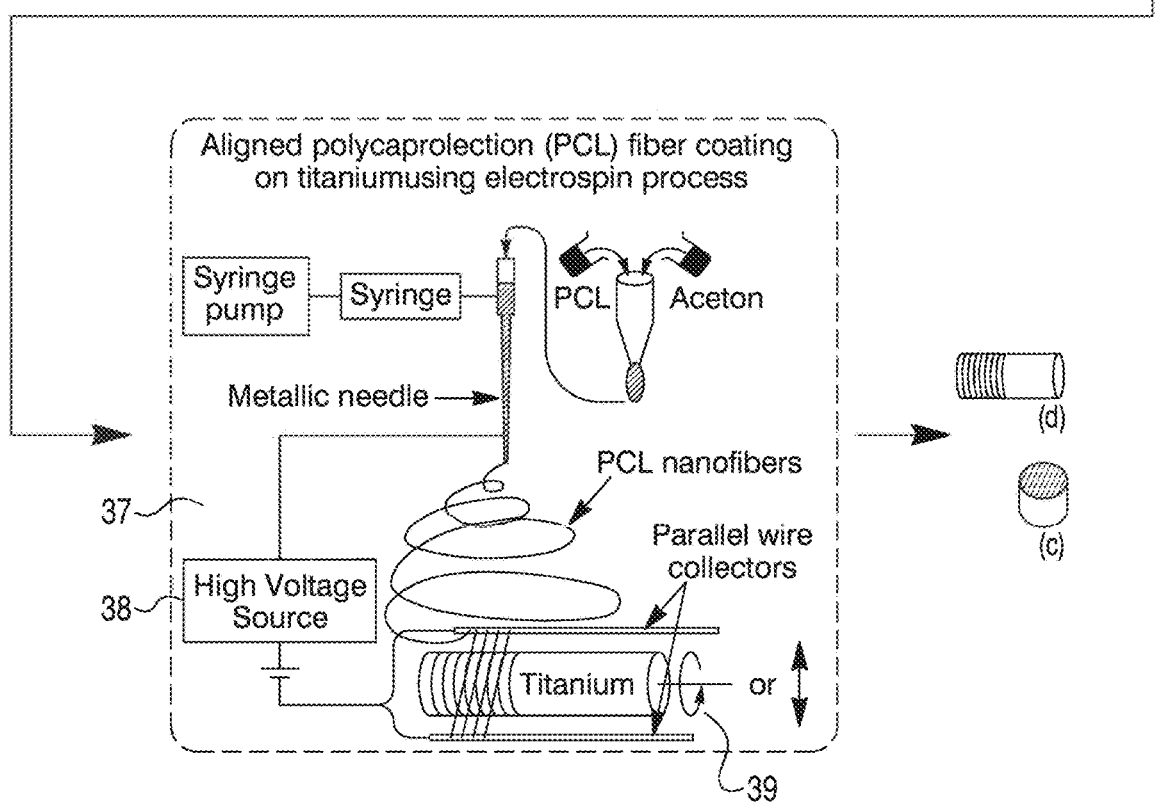

Referring now to FIG. 3, a non-limiting diagram shows the process of the present invention providing a method 30 for creating TiN ridges on a Ti implant and PCL-CG coating on Ti implants having the TiN ridges. The FIG. 3 shows the formation of TiN ridges along the flat end surface of a Ti implant (e.g., 10 mm diameter×6 mm height) and the circumference surface of a Ti implant (e.g., 2.2 mm diameter×12 mm height). In a preferred embodiment, a thin film of Su8 photoresist 31 (available from MicroChem Corp., Westborough, Mass.) is used to cover the Ti surface excluding ridge sites. A mask 32 with channels is placed on the Ti implant and exposed for UV etching 33 to create 3D textures at the sites. Research-grade nitrogen gas (available from AirGas, Inc.) is spattered 34 on the Ti surface to create TiN coating. The TiN ridges are visible upon removal 35 of Su8 by a photoresist removing chemical (e.g., RemoverPG also available from MicroChem Corp). The grooves formed by TiN ridges are coated by NFM made with the application of thin layer collagen 36 and multilayers of PCL ENF 37. FIG. 3 includes the process of coating the implant with multilayers of ENF 37. In a preferred embodiment, PCL solution is prepared by ultrasonic mixing of 7.69 wt % of PCL pellets with acetone. The sonication process is carried out at approximately 80° C. for an about an hour. The PCL solution is poured into a glass syringe in an infusion pump for fiber production. PCL fibers are ejected from the glass syringe via charged needle. The needle is charged by a high voltage power source 38. The fibers are deposited between two parallel collectors (e.g., wires or plates) forming an aligned layer 39. In one embodiment, to collect multiple layers of fiber on a larger diameter (e.g. 10 mm) Ti implant, the Ti implant is brought into contact with the aligned fiber layer positioned between the collectors, then lowered and rotated 90° and the process repeated to collect another layer. To collect multiple layers of fiber on smaller diameter (e.g., 2 mm) Ti implants, Ti implants may be rotated with constant speed using a motorized stage. Rotating larger diameter Ti implants a constant speed provides an alternative method for capturing fiber layers on larger implants.

Figure 4:
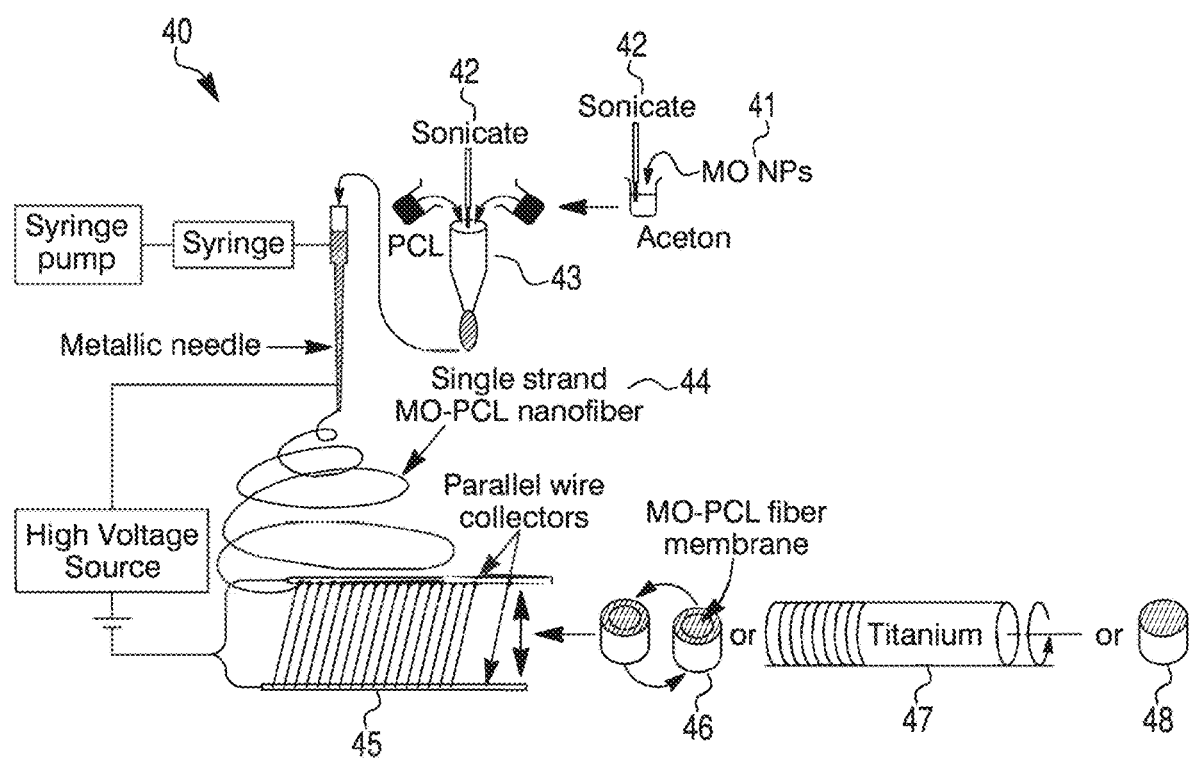
FIG. 4 is a non-limiting diagram showing the schematic representation of process for creating of microgrooves on Ti using machine sawing and depositing MgO nanoparticles immobilized PCL-CG ENF on the Ti.

Referring now to FIG. 4, a non-limiting diagram shows the process of the present invention providing a method 40 for tethering of metal oxide nanoparticles (MO NPs) with a single PCL nanofiber using the electrospin setup depicted in FIG. 3, 37. In a preferred embodiment, PCL solutions with different types of MO NPs are dissolved in acetone 41. Briefly, a 5 wt. % of each kind of NPs may be accurately weighed and sonicated 42 for 30 minutes to properly disperse in acetone. Then, PCL beads are added to the above solution so that the final solution contains 15 wt. % PCL, and the mixture sonicated 42 for another 30 minutes to ensure the dissolution of the PCL pellets and proper mixing with MO NPs. About 10 ml of the prepared solutions with MO-PCL solution may be taken in glass syringes 43 and electrospun 44 individually on two parallel collectors 45 (e.g., wire or plate) to produce aligned MO-PCL NFM. To collect multiple layers of fiber, an acrylic hollow cylindrical substrate 46 may be used to touch the aligned fiber stream, then lowered and rotated 90° and the process repeated to collect another layer on the substrate 46. Multi layers of aligned ENF can be coated on a Ti surface circumferentially by rotating the Ti implant with constant speed 47. Instead of using an acrylic substrate 46, Ti can be used to directly collect fiber on a Ti substrate 48 using the same method used for the acrylic substrate 46.

Figure 5:
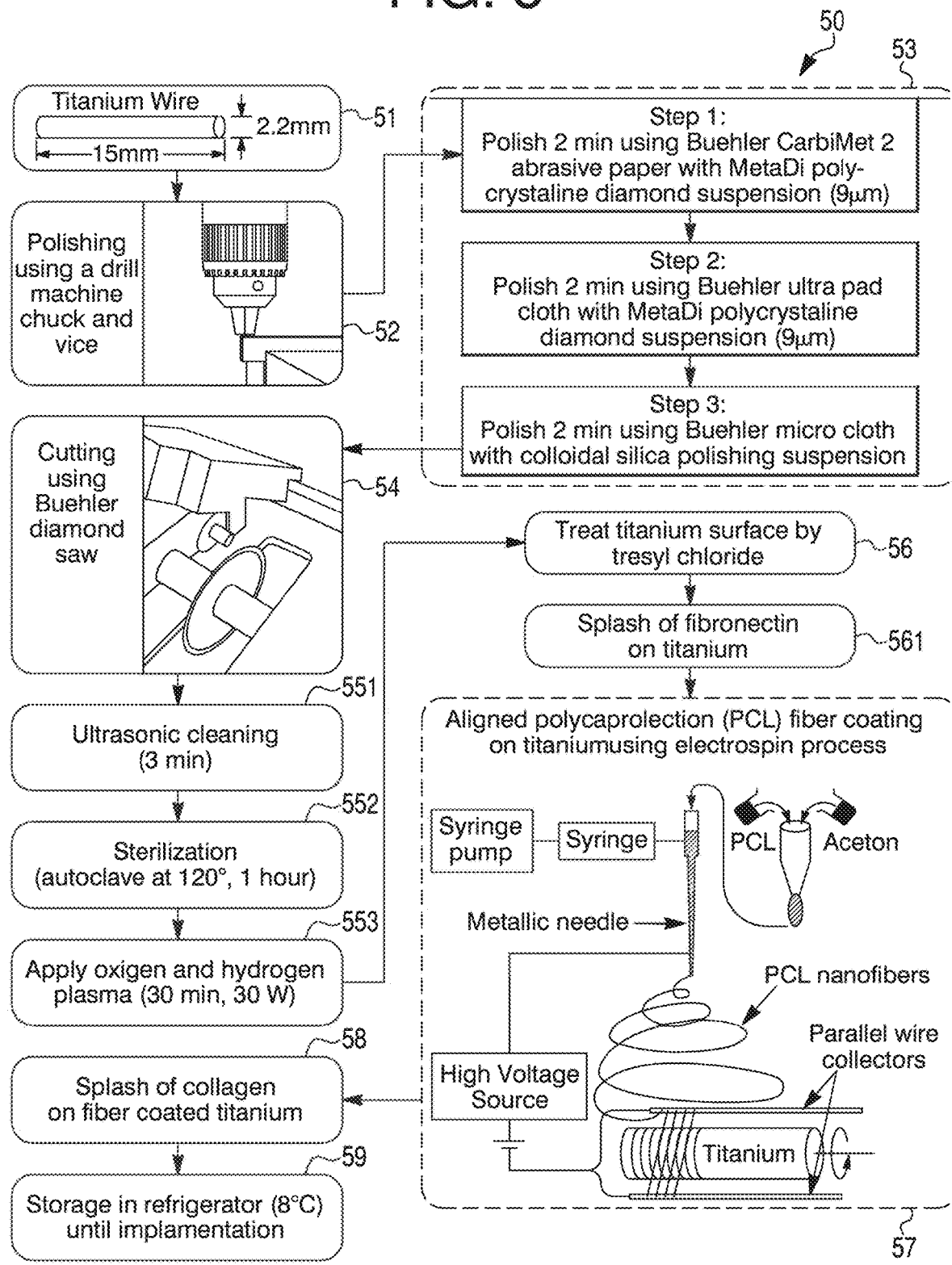
FIG. 5 is a non-limiting diagram showing the schematic representation of process for creating of microgrooves on Ti using machine sawing and depositing fibronectin immobilized Ti and PCL-CG ENF.

Referring now to FIG. 5, a non-limiting diagram shows the process of the present invention providing a method 50 for tethering of cellular fibronectin with titanium (Ti). A Ti implant 51 (e.g., 2.2 mm×15 mm wire) may be polished using a drill machine chuck and gripper 52. Other functionally equivalent rotating devices may be used. A Ti implant may be secured at a drill chuck or by clamps on another type rotating device, and a polish paper (10 mm×50 mm) wrapped around the Ti implant with pressure using the gripper of the drill machine 52. Polishing can occur when the drill machine 52 or other rotating device is in operation. Ti wires samples have been circumferentially polished up to 8 mm from one end using this method. Similar results can be achieved for other cylindrical implants. The three steps polishing technique 53, as recommended by Buehler, Ltd., Evanston, Ill., can be used to polish the Ti implant. Other polishing techniques are possible. A diamond saw blade (Buehler Isomet wafer blade, 0.15 mm thickness, 15HC available from Buehler, Ltd., Evanston, Ill.) may be used to machine the microgroove on the circumferential surface of the implant (e.g., wire) 54. Ti implant (e.g., wire) can be fastened to the shaft of an electric motor or other type rotating machine 54. The motor can be secured in the saw machine 54 at the implant grip holder. Each microgroove can be created by running the motor and saw machine simultaneously in opposite directions for 8 seconds. In one preferred embodiment of the present invention, eighteen bands of circumferential parallel grooves are created starting at a 0.5 mm distance from one end of the Ti wire. The microgrooves are fabricated 0.05 mm apart from each other. The implant (e.g., wire) is then cleaned 551 in an ultrasonic cleaner followed by 70% ethanol wash 552 and autoclaved at 121° C.

The titanium implant surface —OH activity is enhanced by combined application of oxygen and hydrogen in a plasma etcher. The Ti surface is activated 56 by tresyl chloride (2,2,2-trifluoroethanesulfonyl chloride, CF3CH2SO2Cl). Ti is completely covered with Tresyl chloride (TC) and then stored at 37° C. for 2 days. The Ti activated Ti implant is washed with water, water-acetone (50:50), and acetone and dried to produce tresyl chloride (TC) activated Ti surfaces. Human cellular fibronectin is dissolved in phosphate-buffered saline (PBS) solution with pH=7.4 at a concentration of 0.1 mg/mL. The TC activated Ti is immersed 561 into the fibronectin/PBS solution for 24 h at 37° C., then rinsed with double-distilled water. Finally, the Ti surfaces are dried with a gentle stream of dry air to produce FN immobilized Ti. PCL ENF is deposited 57 on the Ti surface described previously. PCL ENF is secured on Ti surface by splashing 58 second layer of FN and air drying the FN in a hood and storing the implant in a refrigerated enclosure 59 until implantation.

The method for PCL ENF coating on titanium with various surface treatments (machined grooves, TiN ridges, FN immobilized) as provided by the present invention provides at least the following unique features:

1. The machined microgrooves for the protection of the PCL ENF coating on Ti from the applied shear loading during the insertion of the Ti in to the bone.

2. The TiN techniques provided by the present invention can be used for both regular and irregular shape implants.

3. Plasma nitridation improves hardness and ductility that may result in an increased transfer of stress to reduce the effect of stress shielding of bone.

4. The use of oxygen and hydrogen plasma for nanoscale surface modification of Ti, is uniquely used to activate the surface of Ti for the attachment of collagen and fibronectin which bonds the PCL ENF on the Ti surface.

5. The effects of the use of MgO nanoparticles with PCL ENG on the implant-bone interaction may be enhanced to provide better mechanical stability and osseointegration.

6. The groove topography for implant that will provide the optimum biomechanical compatibilities of the implant can be controlled.

7. At the groove, other biological glue such as PMMA cement, fibronectin, collagen is used to attach the PCL ENF. Microgroove and Poly(ε-Caprolactone)-Collagen Nanofiber Matrix (PCL-CG NFM) Coating Improve the Mechanical Stability and Osseointegration of Titanium Implant.

Figure 6:
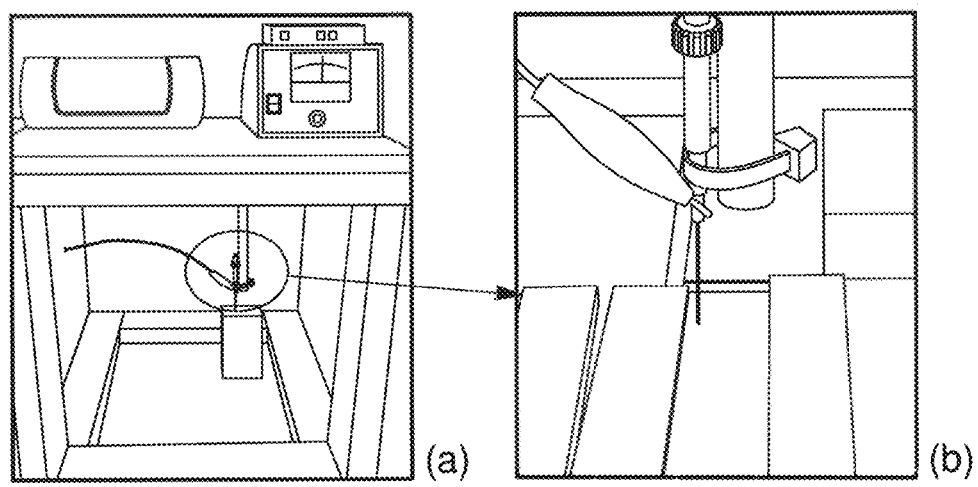
FIG. 6 shows experimental aspects where PCL fiber was produced using ID=0.31 mm gauge needles and ID=0.12 mm gauge needles installed in an electrospin unit by dissolving 5 wt % of PCL beads with acetone, where aligned PCL ENF was collected between two parallel wires.
Figure 7A:
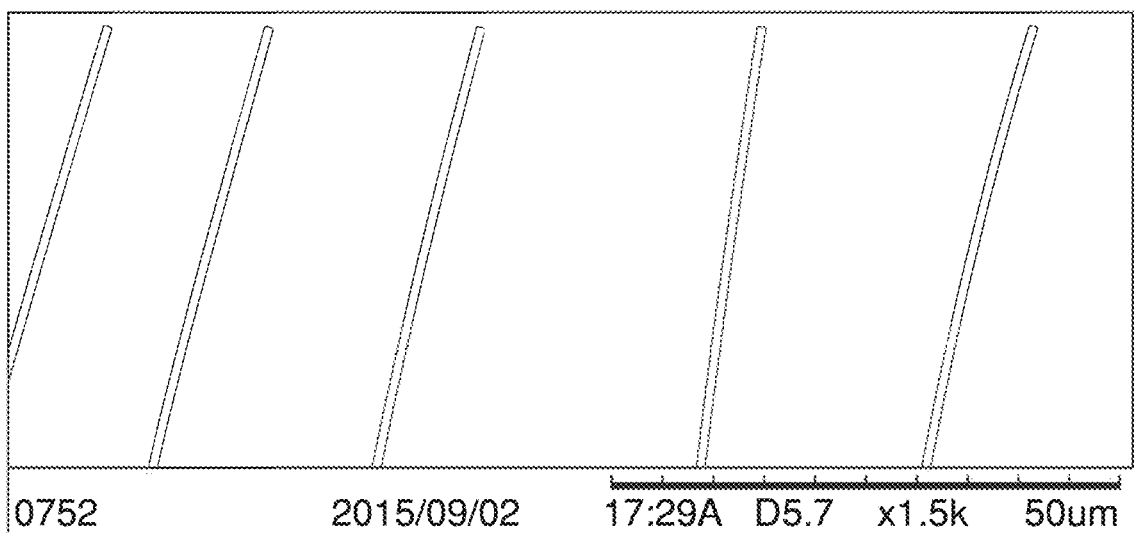
FIG. 7a shows experimental aspects where the average diameters of the fibers found from scanning electron microscope (SEM) images were 518 nm.
Figure 7B:
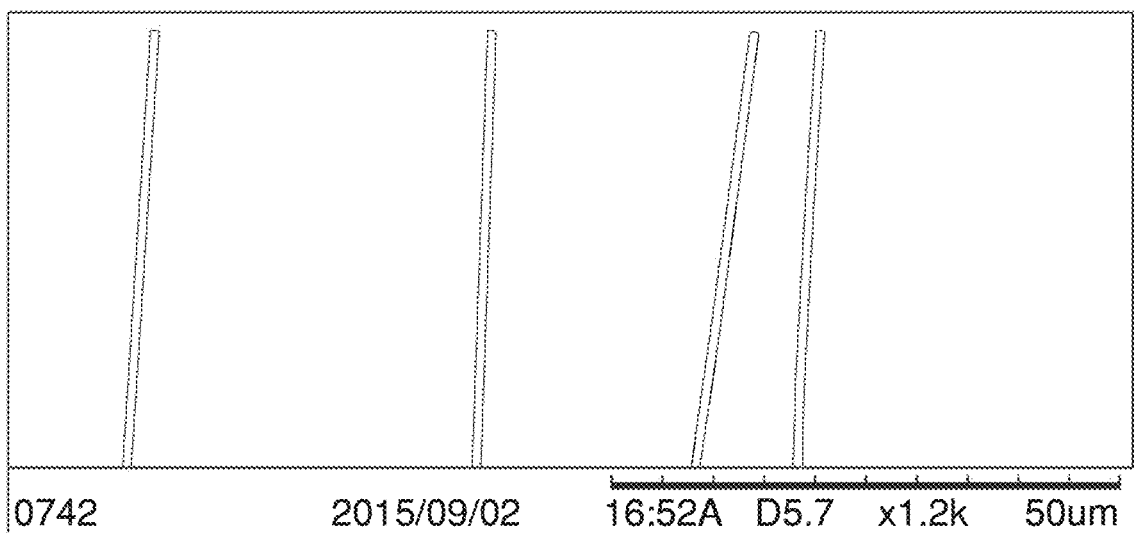
FIG. 7b shows experimental aspects where the average diameters of the fibers found from scanning electron microscope (SEM) images were 305 nm, where the fibers were attached with MgO nanoparticles.

The method of the present invention providing machining of microgroove on Ti and filling the grooves with ECM made with PCL-CG was proven through experimentation by the Applicant to be successful in increasing the in vivo mechanical stability and promoting osseointegration on Ti implants. The automatic production of groove by TiN as disclosed for the present invention increases scalability of the technique for commercialization by optimizing the groove topography using nanofabrication techniques, which will lead to design of better performing clinical implants. Through experimentation, the Applicant developed the methods of the present invention shown in FIG. 6 at (a) and enlarged for viewing at (b). PCL solution may be prepared by ultrasonic (Sonics & Materials, Inc., model #Vibra-cell VCX 130) mixing of 7.69 wt % of PCL pellets (pellet size-3 mm, average Mn 80,000) with acetone (laboratory reagent ≥99.5%). The sonication process may be carried out at approximately 60° C. for 30 minutes. The solution may be poured into a glass syringe in an infusion pump (Harvard Apparatus, mode #PHD ULTRA) for fiber production. PCL fibers may be ejected from the glass syringe via charged needle (23G blunt needle, aluminum hub, 1" length, model #BX 25). The needle may be charged by high voltage power source (Gamma High Voltage Research, Inc., model #ES 30 series). Two different diameters of PCL fiber were produced using (ID=0.31 mm) and (ID=0.12 mm) gauge needles deployed in the electrospin unit (FIG. 5, 57). Aligned PCL ENF was collected between two parallel wires (FIG. 4, 45). The average diameters of the fibers determined from scanning electron microscope (SEM) images were 518 nm (FIG. 7a) and 305 nm (FIG. 7b), respectively. Six layers of aligned ENF were coated on Ti by rotating the Ti rod with constant speed. Ti were implanted into rabbit femur and the mechanical stability was measured by a pullout tension test.

Referring now to FIG. 8, the image shows a fabricated samples with grooves 82 made by machining. The image shows a fabricated samples with grooves made by machining and depositing PCL ENF on the grooves 83. Nanofiber matrix is deposited along the groove 83 to enhance the mechanical stability and osseointegration of the implant with the host tissue and solve the implant poor fixation problem. A set of parallel microgrooves 82 is created on Ti at the circumferential direction to increase the surface area of implant in contact with bone and to protect the NFM made with Polycaprolactone (PCL) electrospun nanofiber (ENF) and collagen at the groove 83 from physiological loading.

Figure 9A:
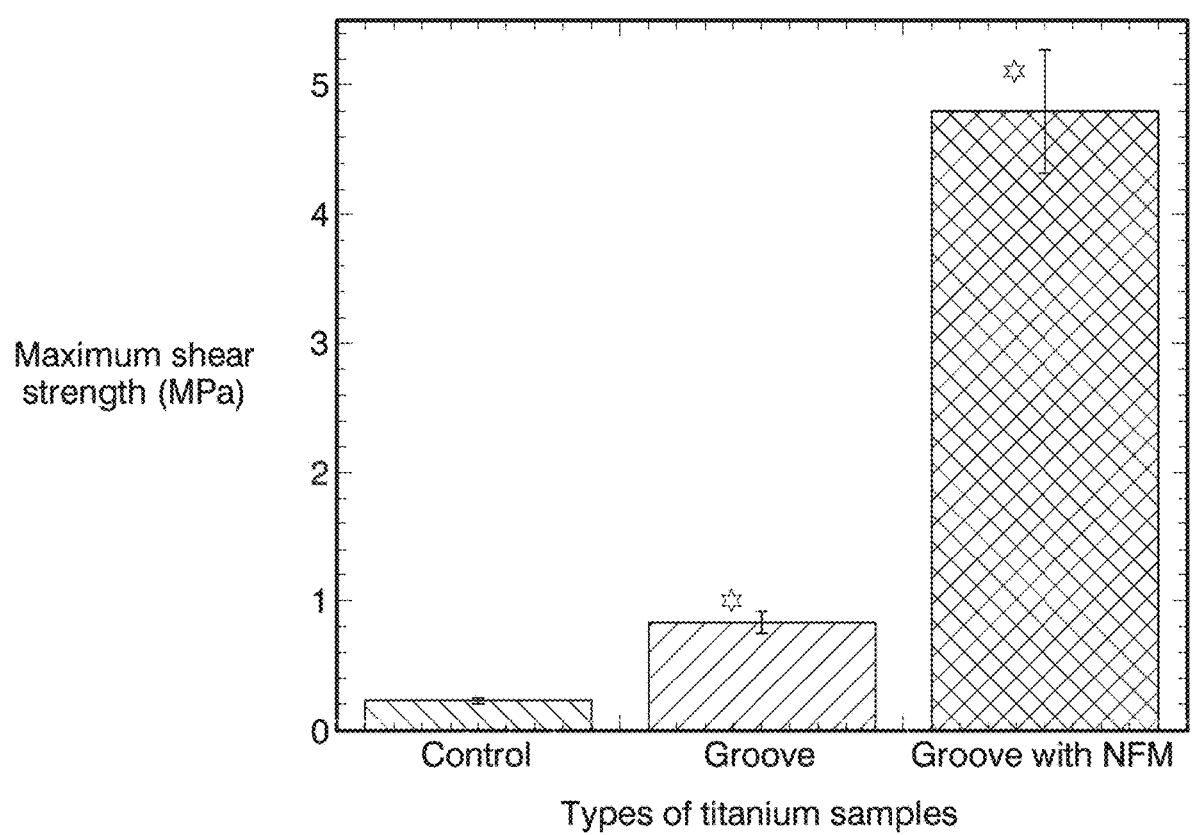
FIG. 9a shows experimental aspects where mechanical test results on in vivo titanium/bone sample show that the amount of force required for breakage of titanium from bone on fiber coated Ti is higher than control and only groove.

Referring now to FIG. 9a, the experimental results show that the mean values of shear strength were 3 times higher for grooved Ti samples (0.84±0.3 MPa, n=6) compared to control samples, (0.26±0.09 MPa, n=6), although the difference was not statistically significant ($p>0.05$).

Figure 9B:
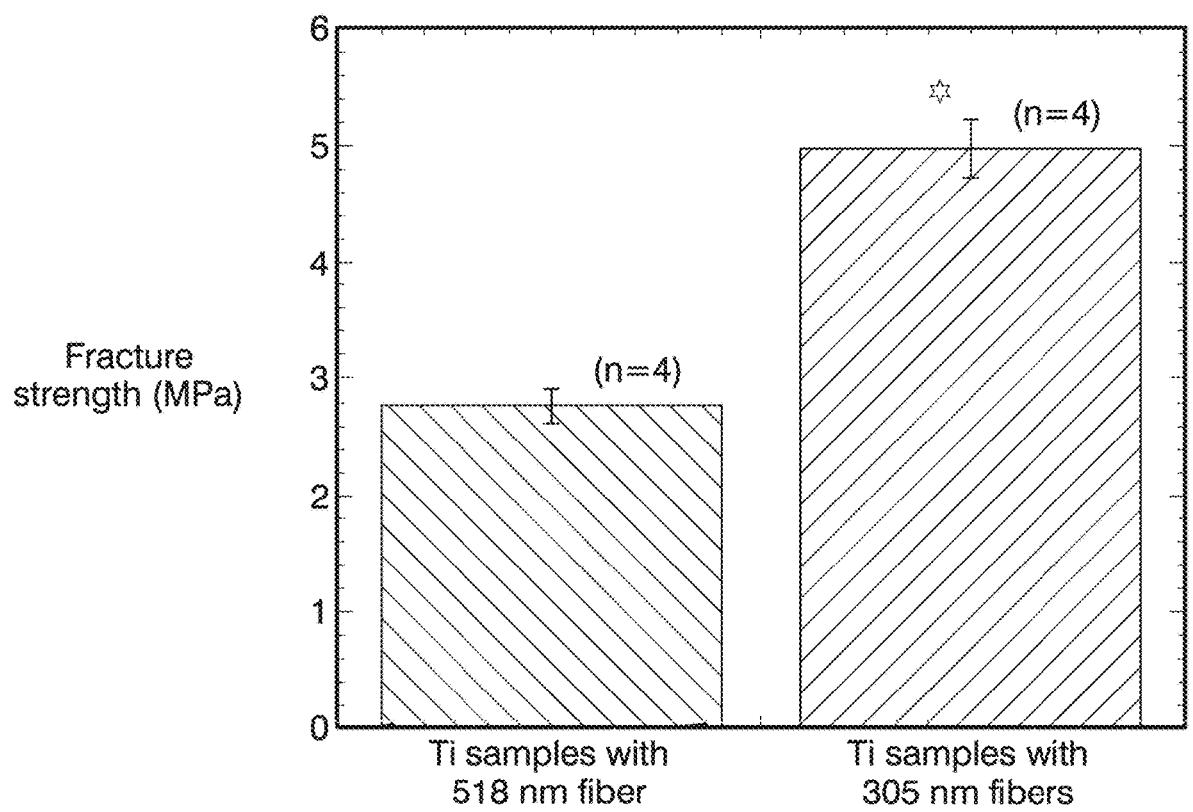
FIG. 9b shows experimental aspects where mechanical test results on in vivo titanium/bone sample show that the amount of force required for breakage of titanium from bone on nanosize fiber coated Ti is higher than micron size fiber coated Ti.

Referring now to FIG. 9b, comparing fracture strength results of grooved Ti samples coated with CG-PCL NFM, demonstrates that the ultimate shear strength of NFM coated grooved samples (4.79±0.39 MPa, n=6) were higher (more than 18 times) compared to control samples ($p<0.05$). No statistically significant differences of diameters among the sample group were observed ($p>0.05$). Also there was no statistically significant differences of the length of implant in contact with bone among the sample group ($p>0.05$). Therefore, the surface coating of Ti samples by CG-PCL NFM had a significant effect on the shear strength of the samples. Pullout tension tests result (FIG. 9b) showed that the fracture strength of Ti samples having groove with 305 nm diameters of nanofiber are 1.79 times higher than Ti samples having groove with 518 nm diameters of nanofiber.

Figure 10:
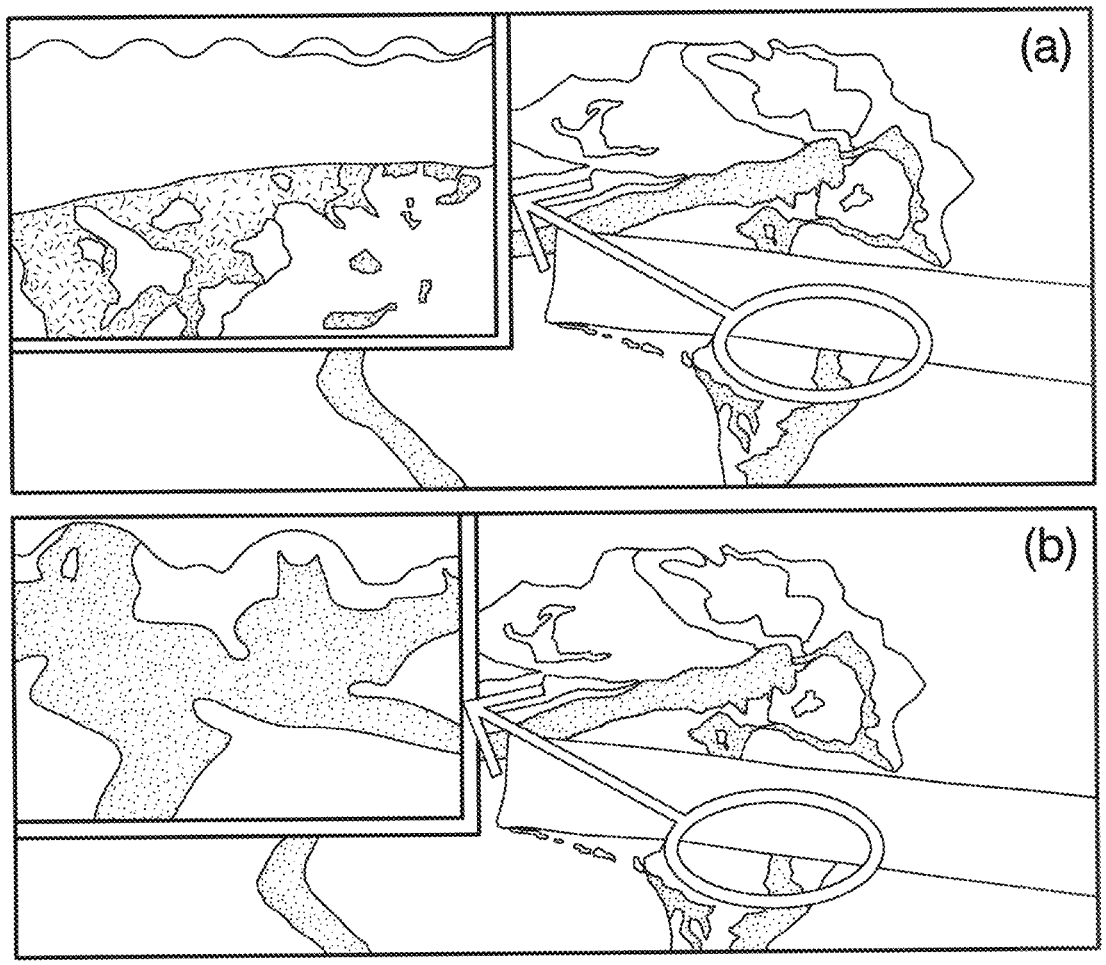
FIG. 10 shows experimental aspects where histomorphometric analysis results (and Table 1) using Sanderson rapid bone stain show that the amount of bone and tissue growth on only groove Ti is less than on (b) grooves with PCL-CG NFM coated Ti.

Referring now to FIG. 10, sectioning, staining, and imaging for histomorphometric analysis was done at pathology core research laboratory in the University of Alabama at Birmingham (UAB). Histomorphometric analysis results (FIG. 10 and Table 1) using Sanderson rapid bone stain show that the amount of bone and tissue growth on ECM coated Ti is higher than control and fiber diameter in ECM has an effect on bone growth. Experimental aspects where staining of uncalcified Ti-bone samples include only grooves as shown in image (a). Experimental aspects where staining of uncalcified Ti-bone samples include groove with 308 nm PCL ENF-CG as shown in image (b). In images, older bone has a lighter gray (pink in color image) and new bone stains dark grey (red in color image), and connective tissue is stained in white. The histological examination shows the total new bone area of a Ti implant significantly increased with the application of PCL-CG NFM.

TABLE 1

Histomorphometric analysis data for a randomly selected Ti sample with only groove; Ti samples having groove with 518 nm and 305 nm diameters of ENF.

| Histological analysis parameters | Only groove | Groove with 518 nm ENF | Groove with 305 nm ENF |
| --- | --- | --- | --- |
| Average Groove Depth (μm) | 75.44 | 50.27 | 71.44 |
| Total Bone to Implant sf. (mm) | 7.20 | 20.61 | 12.69 |
| % Bone to Implant Contact (%) | 39.78 | 90.60 | 62.18 |
| Total New Bone Ar. (mm$^2$) | 0.019 | 0.294 | 0.359 |
| Tt Cortical Bone Ar. (mm$^2$) | 0.000 | 0.262 | 0.149 |
| Cortical Bone Surface (mm) | 0.00 | 7.81 | 3.59 |
| New Bone Surface (mm) | 1.29 | 13.12 | 11.23 |
| Total Tissue Area - ROI (mm$^2$) | 1.84 | 2.17 | 1.939 |
| Tt. BV/TV (%) | 1.01 | 25.63 | 26.18 |
| Tt. New Bone/TV (%) | 1.01 | 13.54 | 18.52 |
| Tt. Cortical Bone/TV (%) | 0.00 | 12.09 | 7.66 |

Figure 11A:
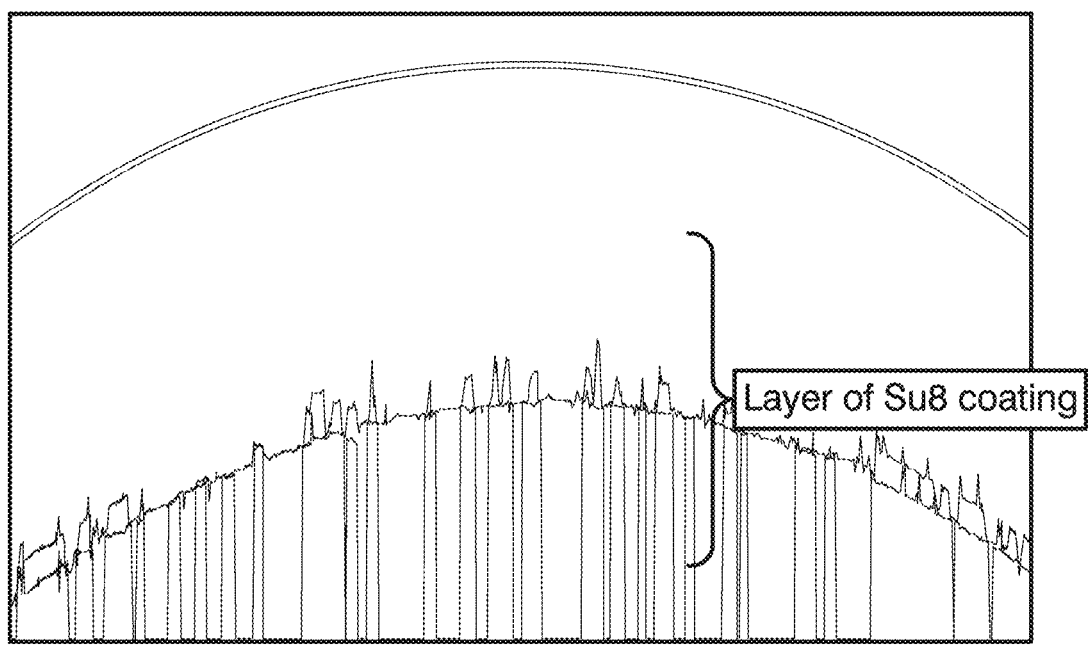
FIG. 11a shows the confocal microscope image of Su8 coated Ti. Su8 coating was applied circumferentially. The figure shows uniform thickness of Su8 coating material.
Figure 11B:
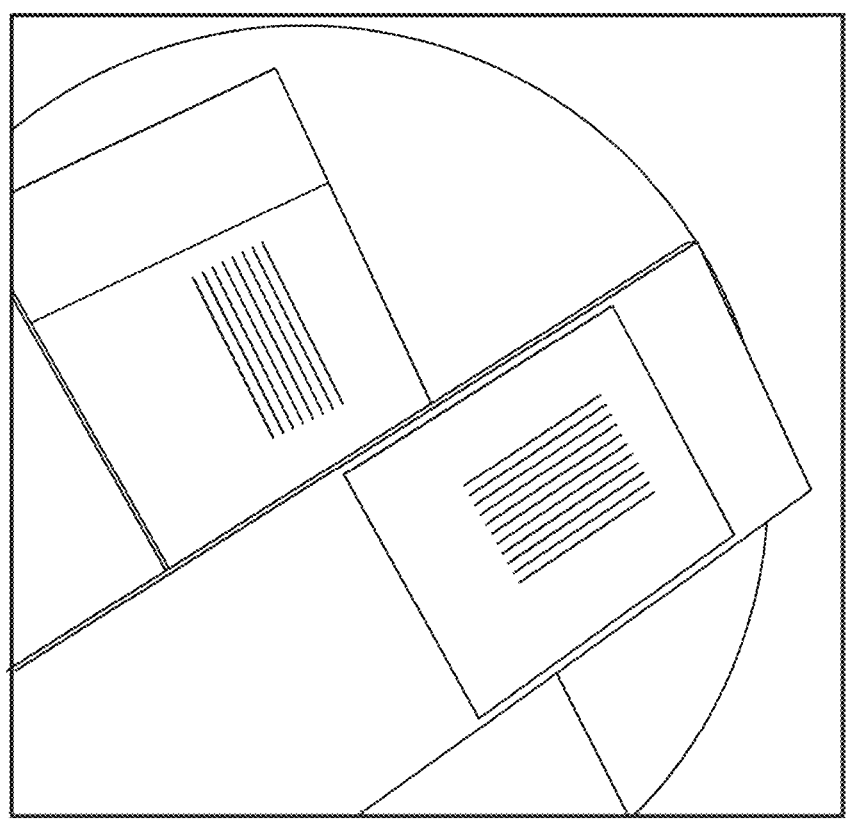
FIG. 11b shows the mask used for creating channels on Su8 coated Ti.
Figure 11C:
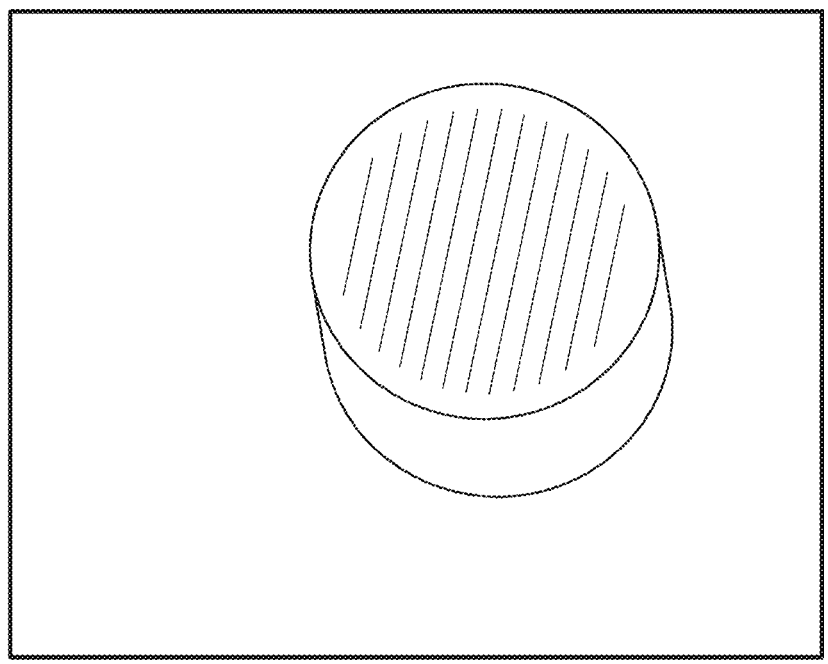
FIG. 11c shows the 3D linear grooves created on the 10 mm diameter Ti surface covered with Su8 coating material.
Figure 11D:
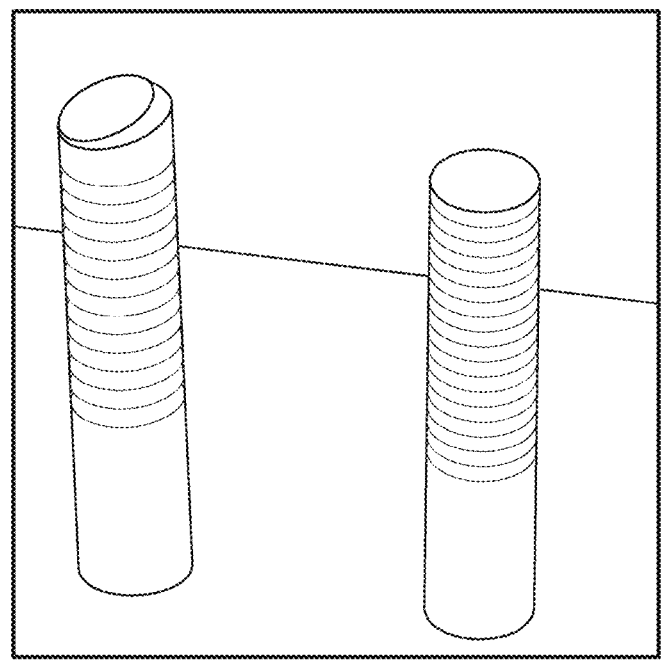
FIG. 11d shows the 3D circumferential grooves created on the 2 mm diameter Ti surface covered with Su8 coating material.

Fabrication of TiN Ridge on Ti:

The process of the present invention was demonstrated to provide a method for fabrication of 50 linear TiN ridges for the 10 mm diameter test samples and 30 circumferential TiN ridges for the 2 mm diameter test samples using photolithography and plasma nitrogen deposition technique (FIG. 3). A 16 μm thin film of Su8 photoresist covers the Ti surface uniformly by spin coating the photoresist on Ti (FIG. 11a). A mask with channels (FIG. 11b) is placed on Ti and exposed for UV etching to create 3D textures at the sites. FIG. 11c and FIG. 11d shows the fabricated 3D Su8 textures on Ti. Research-grade nitrogen gas can be spattered on the Ti surface to create TiN coating. The TiN ridges is visible upon removal of Sub by a photoresist removing chemical (RemoverPG).

Figure 12:
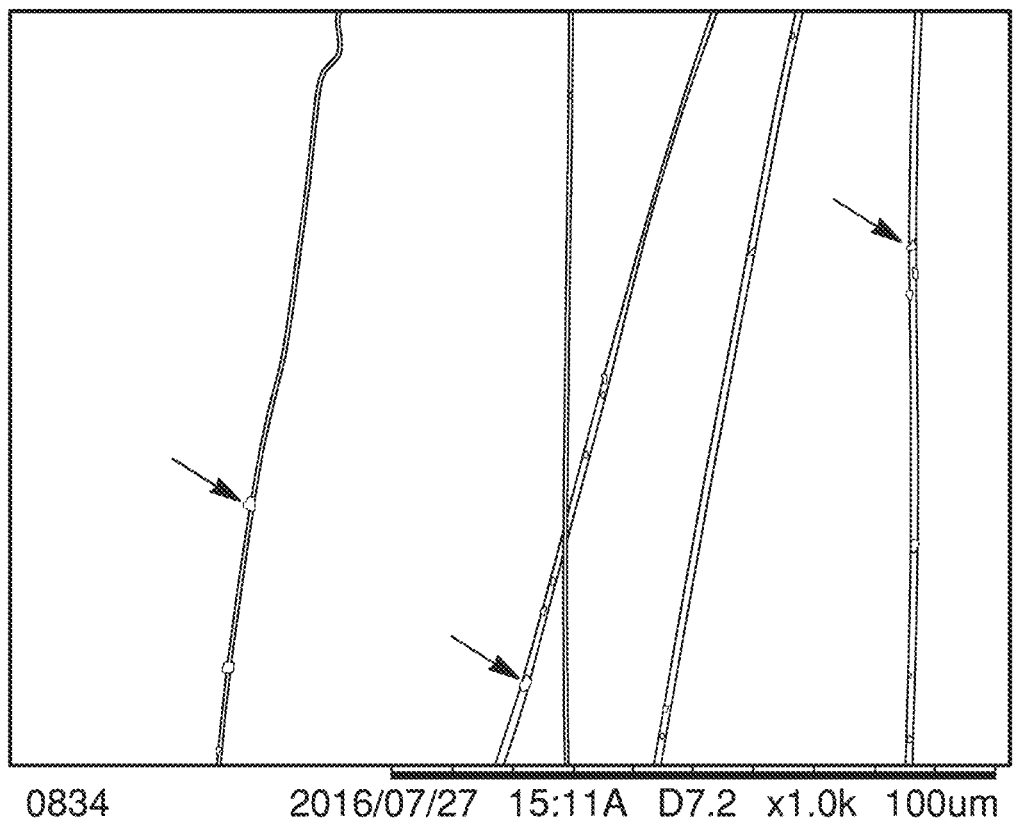
FIG. 12 shows the scanning electron microscope (SEM) image of MgO NP tethered with PCL nanofiber.

Immobilization of MgO NP on PCL ENF:

The process of the present invention was demonstrated to provide a method for fabrication of MgO NP tethered PCL ENF. MgO NPs was dissolved in acetone. A 5 wt. % of MgO NPs was accurately weighed and sonicated for 30 minutes to properly disperse in acetone. PCL beads will be added to the above solution so that the final solution contains 7.9 wt. % PCL and the mixture was sonicated again for 30 minutes. MgO-PCL solution was taken in glass syringes and electrospun. The fibers were collected between two parallel plate collectors. To collect multiple layers of fiber, an acrylic hollow cylindrical substrate was used to touch the aligned fiber stream, then lower it and rotate the substrate 90° and repeat the process to collect another layer. The fiber was viewed under SEM where the tethering of MgO with PCL fiber was clearly visible (marked by black arrows in FIG. 12).

Rat osteoblast cells was cultured in standard culture conditions (37° C. in a 5% CO2 incubator on tissue culture dishes) using DMEM/high glucose+5% FBS and 1% ABAM (Sigma Chemical). Cells were dissociated using 1× trypsin/EDTA solution (Sigma Chemical) for 5 minutes at room temperature, followed by serum inactivation. Cell adhesion, proliferation, differentiation and protein adsorption tests were conducted on PCL-CG NFM and MgO-PCL-CG NFM coated Ti samples. In short, osteoblast cells were seeded at a density of 70,000 cells/ml on each group of Ti samples in a custom-made silicone well-plate. Cells were then cultured for 48 hours to allow cell adhesion and proliferation on the Ti surface. Parallel samples similar to those tested for adhesion and proliferation were cultured for 3 weeks and prepared for immunostaining to determine hydroxyapatite mineralization and osteonectin adsorption. A Click-iT® EdU stain was used to evaluate cell adhesion and proliferation assay for each sample according to vendor's protocol. This 48-hour assay involves the addition of EdU, or 5-ethynyl-2'-deoxyuridine, to each well after the initial 24 hour incubation. The EdU is a modified thymine nucleotide that contains a terminal alkyne 51. After a total of 48 hours, the cells were fixed with paraformaldehyde and stained with Alexa-488. The terminal alkyne in the EdU reacts with the azide in Alexa-488, which cause the proliferated cells that incorporate the EdU tag to fluoresce green under fluorescent microscopy. An OsteoImage™ mineralization assay kit from Lonza was used according to vendor's protocol. For the protein adsorption test, osteonectin was used as the primary antibody (clone AON-1; Developmental Studies Hybridoma Bank) and goat anti-mouse rhodamine (red) was used as the secondary antibody. For proliferation, mineralization, and protein adsorption tests, nuclei were counterstained with DAPI stain (blue). The qualitative and quantitative measurements of cell viability on the treated Ti surfaces was conducted from images captured with an Olympus DP72 camera and CelSens software. Cell adhesion on the surface of all types of Ti samples was analyzed for the qualitative measurement of cell viability. The number of cells adhered and the number of cells proliferated after adhesion to each sample was determined from the captured images using the ImageJ software program (http://imagej.nih.gov/ij/). Cell densities on NFM-coated Ti samples was compared to the control Ti samples for the quantitative measurement of cell adhesion and percentage of proliferation. The ratio of mineralized and osteonectin stain area over total area of the image field was used to compare mineralization and osteonectin activities between control and NFM coated Ti samples, respectively. To identify focal adhesion structures, samples were cultured in the same conditions as for the proliferation and differentiation stains; however, upon harvest the samples were fixed using 3% paraformaldehyde and 0.2% Triton-X-100 prior to staining. Samples were stained for 1 hour with mouse anti-human vinculin (clone h-VIN1; EMD Millipore Sigma), followed by a secondary goat anti-mouse Alexa 488 (Thermo Fisher Molecular Probes). Stained samples were inverted onto large coverslips for visualization using 100× oil immersion on an Olympus IX-71 microscope. Images were captured using an Olympus DP72 camera equipped with CelSens software. Subsequent quantification was done using ImageJ software using a published protocol 48 with modifications (manuscript in preparation).

Figure 13A:
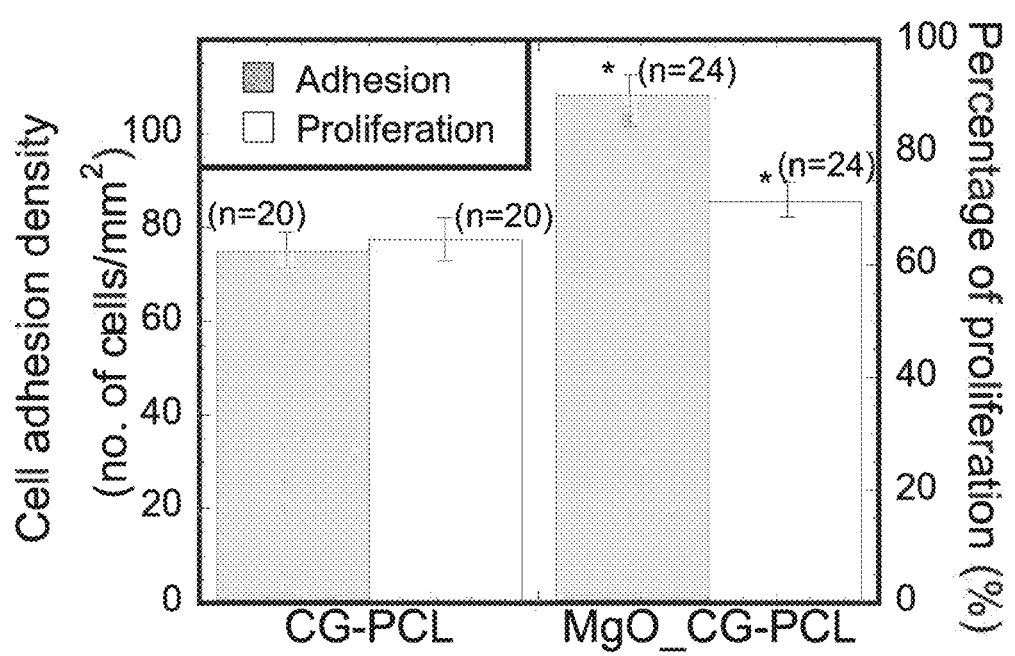
FIG. 13a shows the cell adhesion/proliferation results of the in vitro cytocompatibility test of MgO NP incorporated PCL-CG NFM. In the image * means p<0.05 compared to CG-PCL.
Figure 13B:
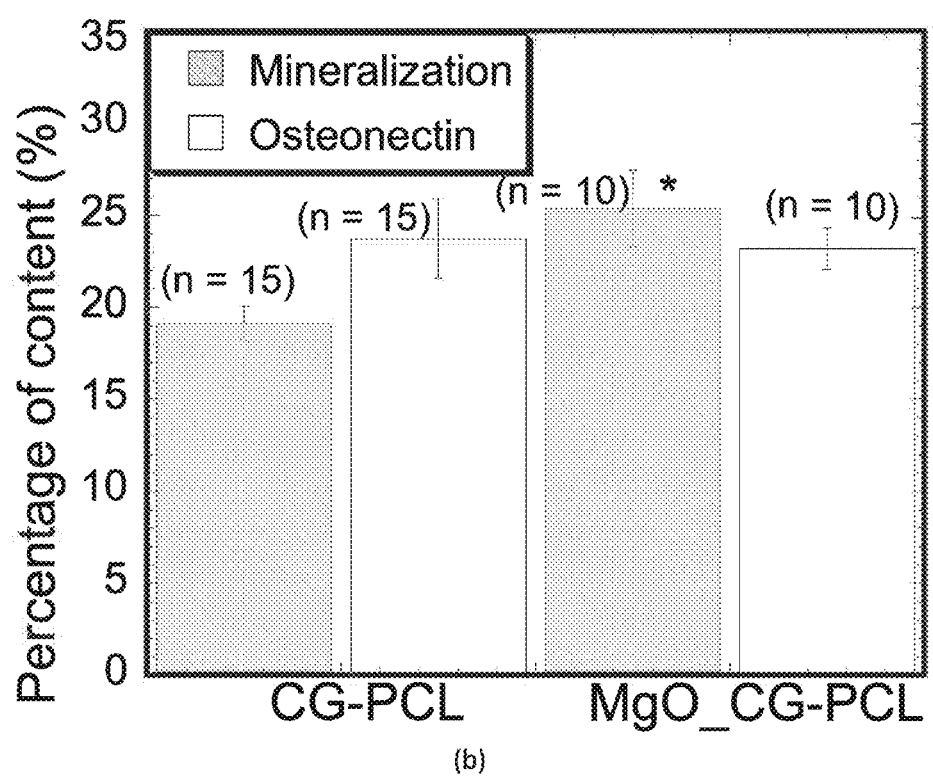
FIG. 13b shows the mineralization/protein adsorption assay results of the in vitro cytocompatibility test of MgO NP incorporated PCL-CG NFM. In the image * means p<0.05 compared to CG-PCL.

The experimental results indicate that cell adhesion/proliferation (FIG. 13*a*), and mineralization/protein adsorption (FIG. 13*b*) of MgO NP added CG-PCL NFM coated Ti was significantly higher compared to CG-PCL NFM ($p<0.05$). Mechanical results showed that shear strength of Ti with bone for MgO added CG-PCL NFM coated (5.97±0.65 MPa, n=6) was higher compare to fracture strength of Ti CG-PCL NFM (4.79±0.39 MPa, n=6) ($p>0.05$).

Figure 14:
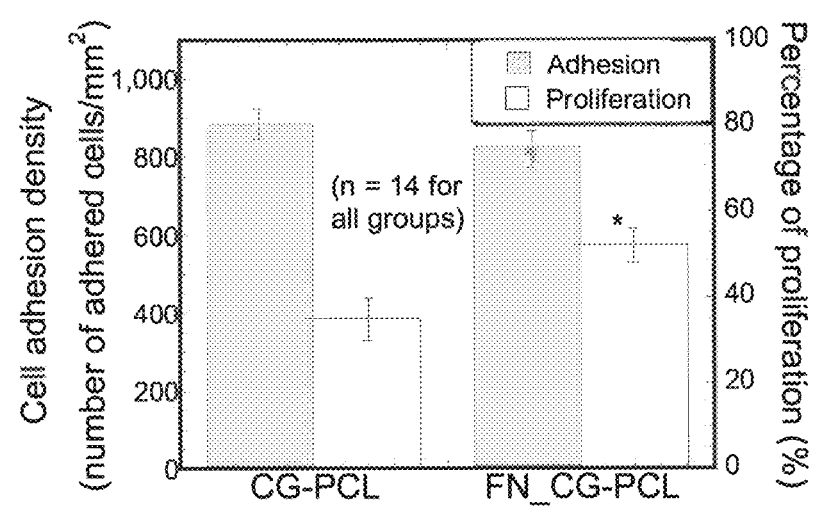
FIG. 14 shows the in vitro osteoblast cell adhesion and proliferation test results of PCL-CG NFM coated Ti without and with FN.

Immobilization of Fibronectin on Ti:

The process of the present invention was demonstrated to provide a method for immobilization of FN on Ti surface using the process as shown in FIG. 5. FN is a multifunctional protein most abundantly found in the extracellular matrix (ECM) under dynamic remodeling conditions such as bone healing and development. FN serves as a biological glue mediating interaction between cells and ECM proteins. FN contains a CG binding domain, so it can be polymerized into CG-PCL NFM. FN has a large binding domain for attaching growth factors such as bone morphogenetic protein (BMP) and transforming growth factor (TGF). Cell viability tests were conducted on CG-PCL NFM coated samples with and without the plasma FN coating on Ti according to the same method as discussed above. Results showed reduced amount of cell attachment ($p>0.05$), but significant improvement of cell proliferation in NFM due to FN coating on Ti ($p<0.05$) (FIG. 14) suggesting that FN coating on Ti can further improve the biological functions of our NFM.

Methods disclosed in related art attempt to improve osseointegration by direct attachment of osteoinductive nanoscale topographies on an implant surfaces. The main concern related to coating nanoscale materials onto an implant surface is the risk of coating detachment and toxicity of related debris. The present invention provides a set of steps (e.g. grooving and oxidizing) by which a nanofiber matrix (NFM), composed of collagen (CG) and poly-ε-caprolactone (PCL) electrospun nanofibers, can be coated on a titanium (Ti) implant without subsequent detachment. An unexpected significant improvement in osseointegration of CG-PCL NFM-coated Ti over non-coated Ti was observed in our laboratory experiments. The advantage of functional coating treatment on an implant is that it is simple, indirect, scalable, inexpensive, and supplementary to other surface treatment techniques. Such treatment can be applied on an implant surface without affecting other implant factors, such as mechanical, medication (e.g. drugs, irradiation), and patient (e.g. age, osteopenia) factors. The biological properties of a functional coating were found to be further improved by local delivery of biomolecules to create a truly osteoinductive platform at the implant/bone interface. Local drug delivery can attain more than a hundred times higher concentration of the drugs in surgical implant sites than a systemic drug regimen. The present invention provides a unique approach of local delivery of biomolecules on a Total Joint Replacement (TJR) implant surface using a nanofiber membrane (NFM).

The motivation for the present invention stems from our in vitro and in vivo evidence that coating bone cement with poly-ε-caprolactone nanofiber mesh (PCL NFM) improves the biocompatibility and osseointegration of cemented titanium implants. Bone morphogenetic protein-2 (BMP2) plays an important role in regulating osteoblast differentiation and subsequent bone formation. We have successfully immobilized BMP2 on PCL NFM by using plasma fibronectin (FN) in our earlier studies. FN is a glycoprotein of the extracellular matrix that also serves as a biological glue, mediating interaction between cells and extracellular matrix proteins. No study has reported the effect of coating PMMA with BMP2-immobilized PCL NFM on the biomechanical performances of PMMA-cemented implants. The present invention provides methods for attachment of BMP2 on a PMMA-cemented implant using PCL NFM for the improvement of biological and mechanical performance of cemented implant surgeries. Immobilization of BMP2 with PCL NFM (referred as BMP2-PCL) and subsequent anchoring PMMA with bone by BMP2-PCL leads to greater in vitro and in vivo osteogenic functions in comparison to PMMA-cemented implants due to higher biological compatibility of the BMP2-PCL-coated cemented implant (referred as BMP2-PCL-PMMA). The present invention can be applied to at least three groups of PMMA-cemented implant-bone interfaces: (I) PMMA, (II) PCL-PMMA, and (III) BMP2-PCL PMMA, as shown in FIG. 15 for a TKR.

Figure 15:
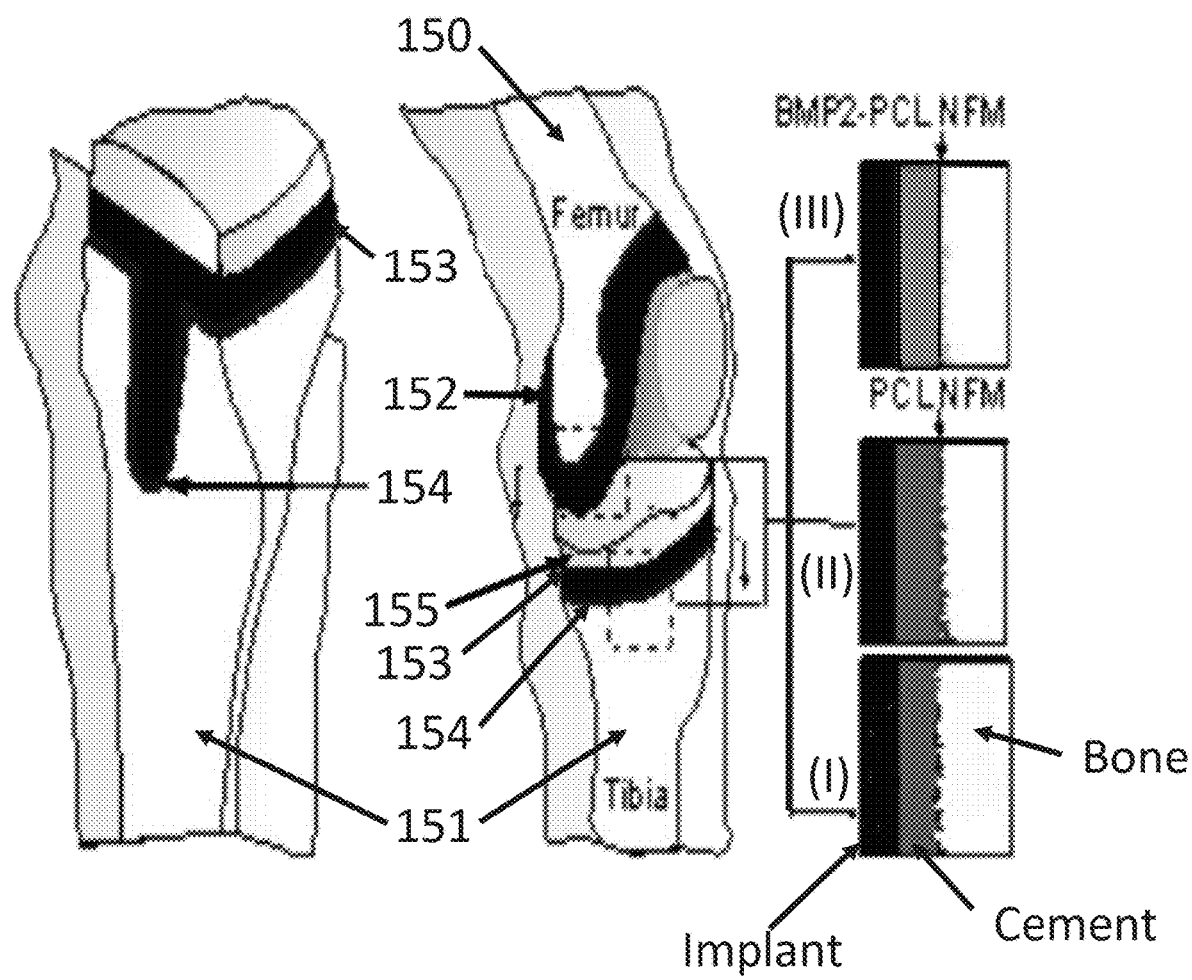
FIG. 15 shows schematic representations of the cemented total knee arthroplasty: (center) full view and (left) cross-section view of tibia prosthetic components, and three groups of cemented implant-bone interface models: (I) PMMA, (II) PCL NFM and (III) BMP2-PCL NFM.

Referring to FIG. 15, during implantation, the TJR implant body is strongly pushed into the Femur 150 and into the Tibia 151: Femoral Implant 152 into the Femur 150 and Tibial Implant 153 into the Tibia 151. These implants are typically cemented 154 to the bone. A plastic bearing 155 separates the Femoral Implant 152 from the Tibial Implant 153. The main challenge of NFM coating on TJR implant (151, 153) is that practically nanofibers attach poorly on the implant surface. When pushed to the bone, fiber comes out from the implant surface. Creating microgrooves on implant surface and securing the NFM at the microgrooves has been invented in our research. Surface cutting, etching, and ion deposition techniques, are suitable to create microgrooves on a cylindrically-shaped implant. These techniques are challenged when applied for controlled fabrication of grooves on a complex shaped implant, such as TJR implants for hips and knees. The present invention overcomes that challenge.

Titanium (Ti) is commonly used materials for TJR surgeries. The shortcoming of Ti is that it is bio-inert material. The direct structural integration of Ti implant with bone occurs due to the surface porosity of the implant surface. The purpose of NFM coating on Ti is that modified Ti surface must attract bone ingrowth to Ti implant surface and at the same time reduce the macrophage-associated inflammation. The NFM on implant surface need to be functionalized for bone ingrowth and reduce the macrophage-associated inflammation on the implant. These above challenges for NFM coating on TJR implant has been solved by the present invention. The present invention provides a set of unique steps/process (FIG. 23) to functionalize the TJR implant surface using nanofiber matrix (NFM). The developed techniques resulted from the discovered limitations and challenges experienced in laboratory experiments directed to producing microgrooves in Ti implants exhibiting complex shapes.

The present invention provides a method (FIG. 23) for laser- and nanofiber-assisted immobilization of biomolecules on cementless Total Hip Replacement (THR) implants: non-grooved THR, laser-grooved THR (LTHR) and biomolecule immobilized PCL NFM coated LTHR (B-PCL-LTHR). A suitable femoral head and acetabulum components may be selected from radiographed images. THR femoral stem may be designed from the estimated femoral canal, head and acetabulum dimension from a developed computational design schemes. The THR implants may be manufactured using a CNC machining (e.g., Haas VF 3) from a metal bar. The top surface of a polished THR implant is treated with 2,2,2-Trifluoroethane-sulfonyl chloride at 36° C. for 48 hours, then washed with water, water-acetone (50:50), and acetone. The implant is then dried and stored in a desiccator. The implant is treated for 24 hours at 37° C. with extracellular matrix protein (collagen or fibronectin) diluted in phosphate-buffered saline (PBS) solution to a concentration of 0.1 mg/mL. The THR implant without any further treatment is non-grooved THR. A set of continuous microgrooves (100 μm width, 100 μm depth, and 200 μm spacing between grooves) is engraved on THR using a fiber marking laser system for making LTHR samples. Laboratory experiments created such microgrooves on Ti6A14V implants to determine the number of nanofiber layers that can reside in the microgrooves during push-in and push-out tests in a press-fitted hole. Our experiments found that nanofiber layers can reside in the grooves.

Figure 16:
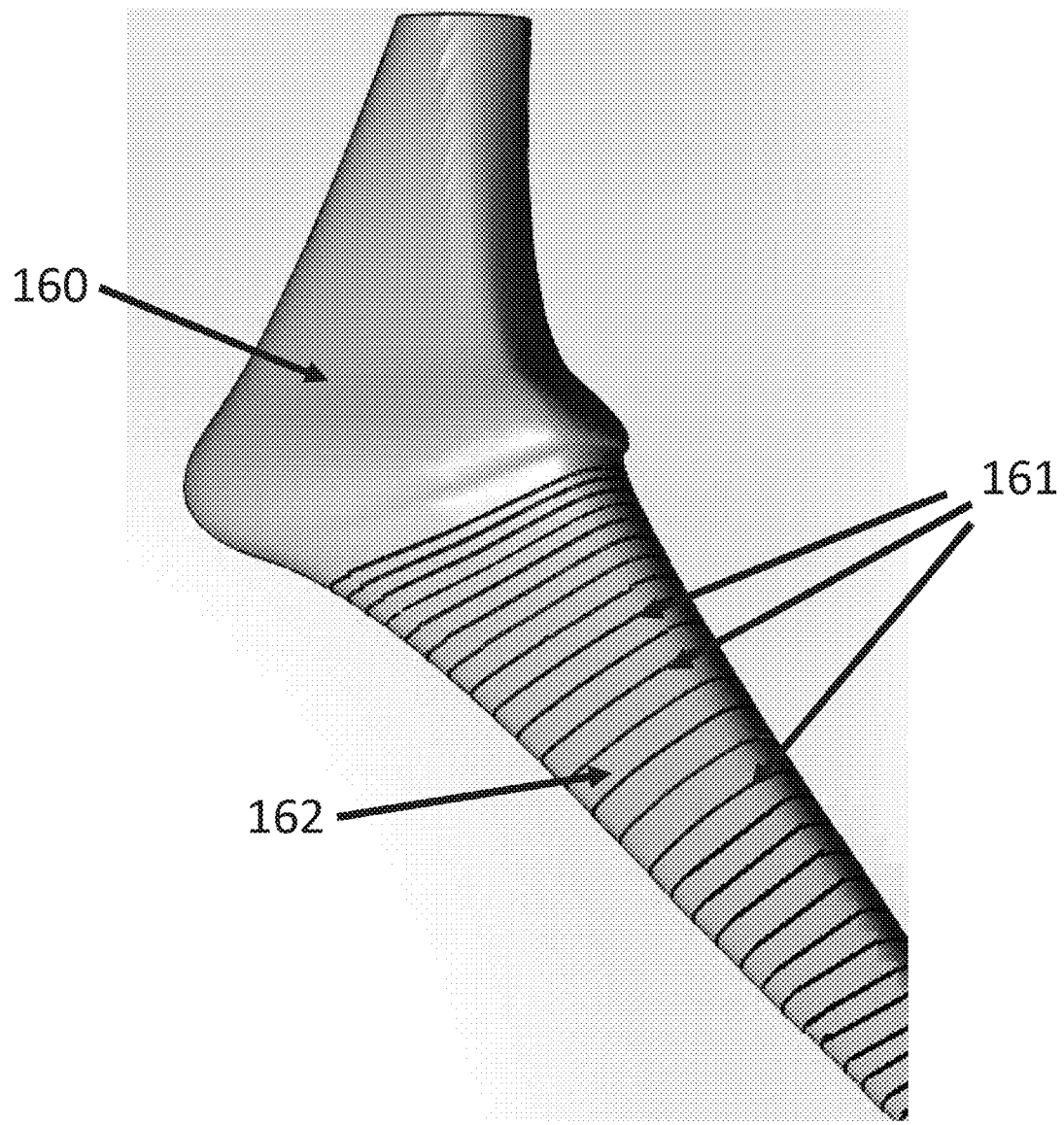
FIG. 16 shows a non-limiting schematic representations of circumferential laser-induced microgrooves on a Ti6A14V titanium alloy SSF femoral stem.

Referring to FIG. 16, a non-limiting schematic shows a representation of circumferential laser-induced microgrooves 161 on a Ti6A14V titanium alloy SSF femoral stem 162. The laser microgrooves 161 are positioned and oriented proximally by 60° from the normal direction of the stem 161 surface because such groove orientation generates maximum stress distribution from implant to the adjacent bone. The surface of LTHR 160 is cleaned in an ultrasonic bath and autoclaved. The surface of LTHR 160 is activated by tresyl chloride and then functionalized with CG according to same method applied to prepare control samples. Either the parallel wire collectors approach shown in FIG. 17 or single disc implant coating approach shown in FIG. 18 can be used successfully to collect aligned fibers on the LTHR 160 surface. Other methods are possible and anticipated. For making B-PCL-LTHR, PCL electrospun nanofiber is deposited on a collagen or fibronectin activated LTHR 160 using an electrospun fiber process. The details of the fabrication of the PCL electrospun nanofiber can be found in U.S. patent application Ser. No. 15/467,652. PCL NFM is collected on hip implant with sufficient thickness not greater than 10 μm, which depends on the depth of the microgrooves 161. The reason for adapting this coating method on a femoral hip stem 162 is due to fact that such a method should be able to maintain controlled and homogeneously-distributed PCL NFM on the implant surface. Different biomolecules (e.g. BMP-2, glutathione, MgO nanoparticles) immobilized PCL NFM complexes can be prepared separately using the methods discussed herein and gently splashed on the PCL NFM coated LTHR implants to prepare corresponding B-PCL-LTHR implants. PCL NFM can be collected on the LTHR stem 161 from a parallel wire collection method (FIG. 17) or using a single disc nanofiber collectors (FIG. 18). In one embodiment, THR implants are prepared under sterile conditions and kept for 30 minutes in a portable ultraviolet sterilizer before surgery.

Referring now to FIG. 19, a non-limiting schematic shows representations of the application of a laser microgrooving on tibial and femoral trays used in a TKR surgery: (FIG. 19A) Bottom and side views of the tibia tray 191 without microgrooves, (FIG. 19B) Bottom and side views of the tibia tray 192 with laser microgrooves, (FIG. 19C) cross-section view of the femoral tray 193 without microgrooves, and (FIG. 19D) cross-section view of the femoral tray 194 with laser microgrooves. The present invention provides a method for laser- and nanofiber-assisted immobilization of biomolecules on cementless Total Knee Replacement (TKR) implants: non-grooved TKR, laser-grooved TKR (LTKR) and biomolecule immobilized PCL NFM coated LTKR (B-PCL-LTKR). An x-ray image of each knee joint may be examined to select an appropriate tibia and femoral trays size for the TKR surgery. A commercial TKR implant or custom made TKR implant components without any further treatment is non-grooved TKR. A set of continuous microgrooves (depth=100 μm, width=100 μm, space between adjacent two grooves=100 μm) along the bottom flat surfaces and around the circumference of the tibial and femoral tray keels are engraved using a fiber-marking laser system (FIG. 19B and FIG. 19D).

Figure 20:
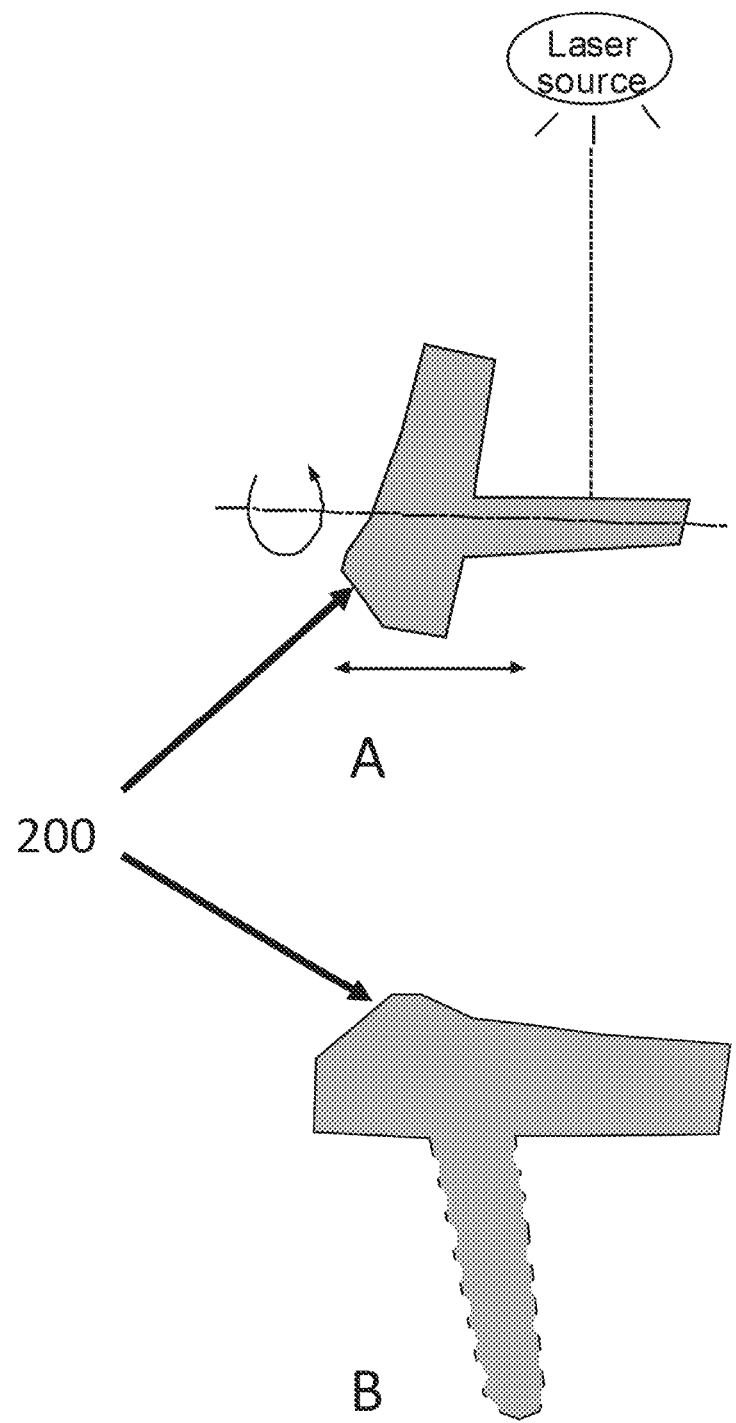
FIG. 20 shows non-limiting schematic representations of (A) microgrooving on tibia tray keel using laser and (B) resultant microgrooves on tibia tray keel due to laser engraving.
Figure 26A:
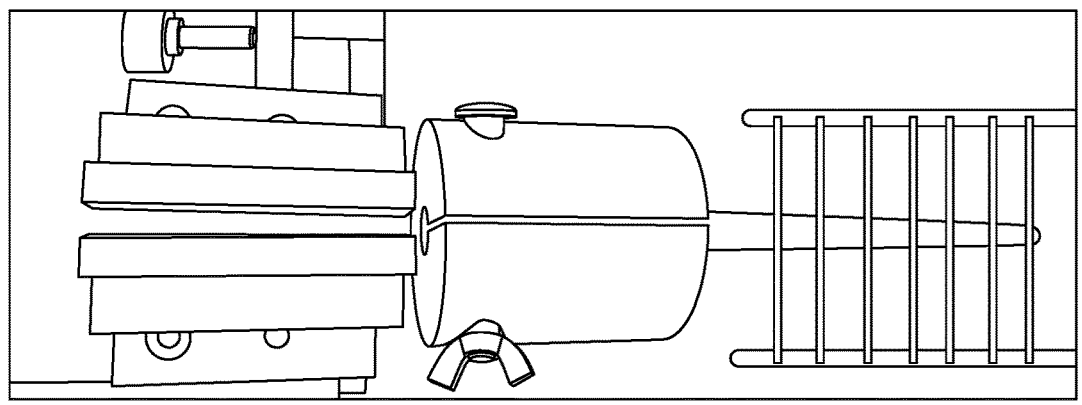
FIG. 26 shows a non-limiting clamp designed to hold a THR implant during coating with NFM.
Figure 26B:
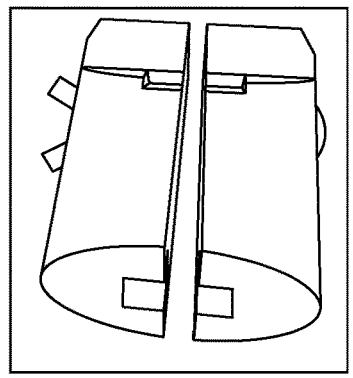
Figure 26C:
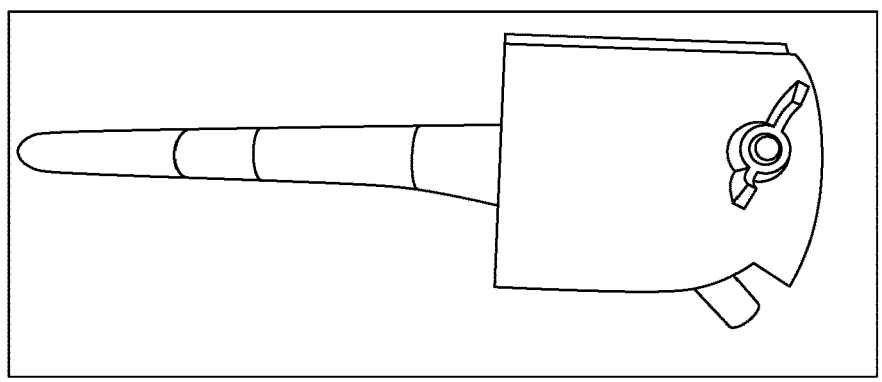

Referring to FIG. 20, a schematic representation is shown depicting (A) microgrooving on a tibia tray keel 200 using laser and (B) resultant microgrooves on the tibia tray keel 200 due to laser engraving. For TKR implant, a similar set of continuous microgrooves (depth=100 μm, width=100 μm, space between adjacent two grooves=100 μm) around the circumference of the tibia tray keel 200 can be engraved using a fiber-marking laser system. The present invention provides an adapter (FIG. 26) designed to grip the tibia tray with the motor shaft for laser engraving on keel surface.

Figure 21:
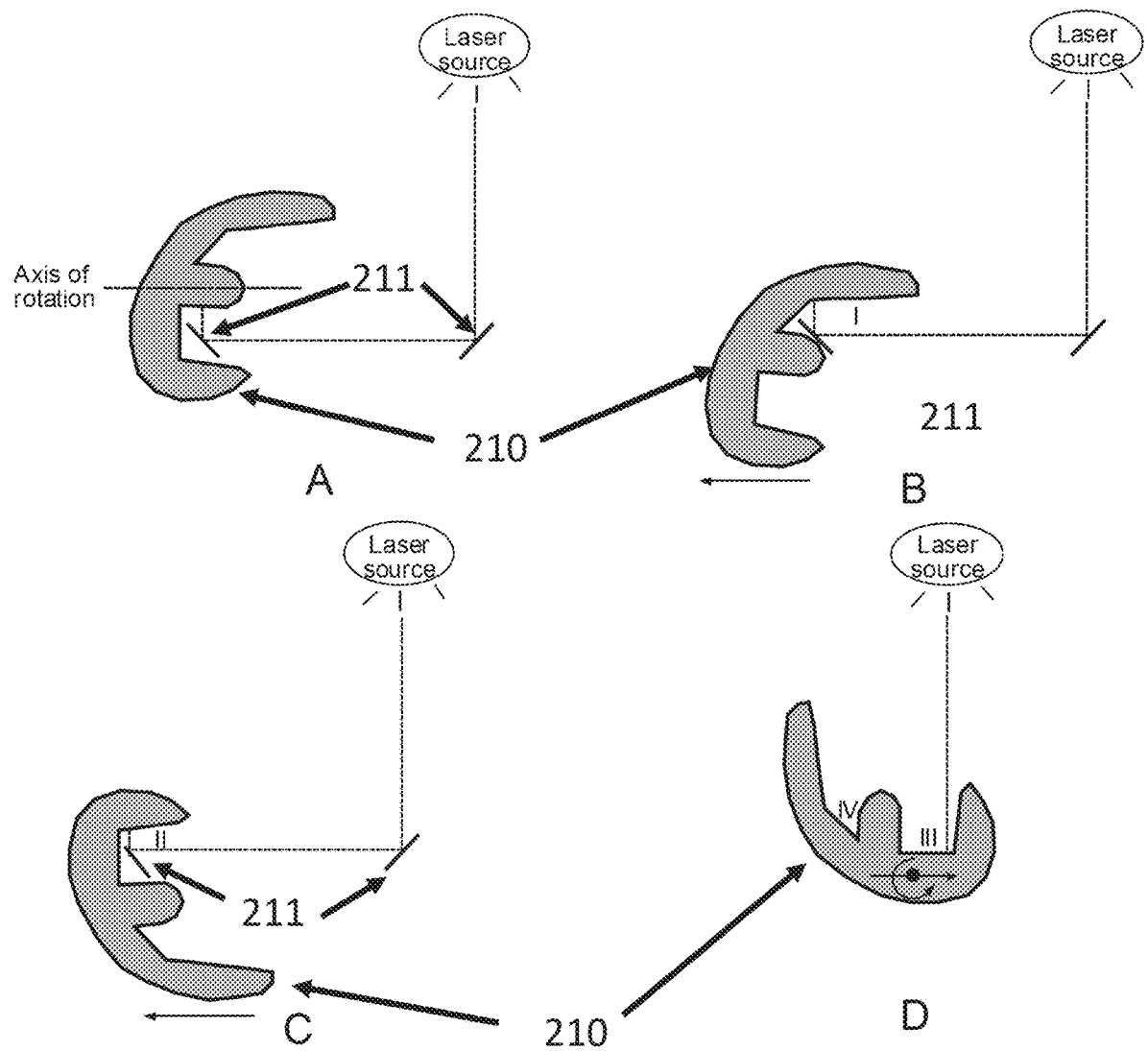
FIG. 21 shows a non-limiting schematic representation of mirror, rotary, and translation stage components to create microgrooves on a femoral tray.
Figure 22:
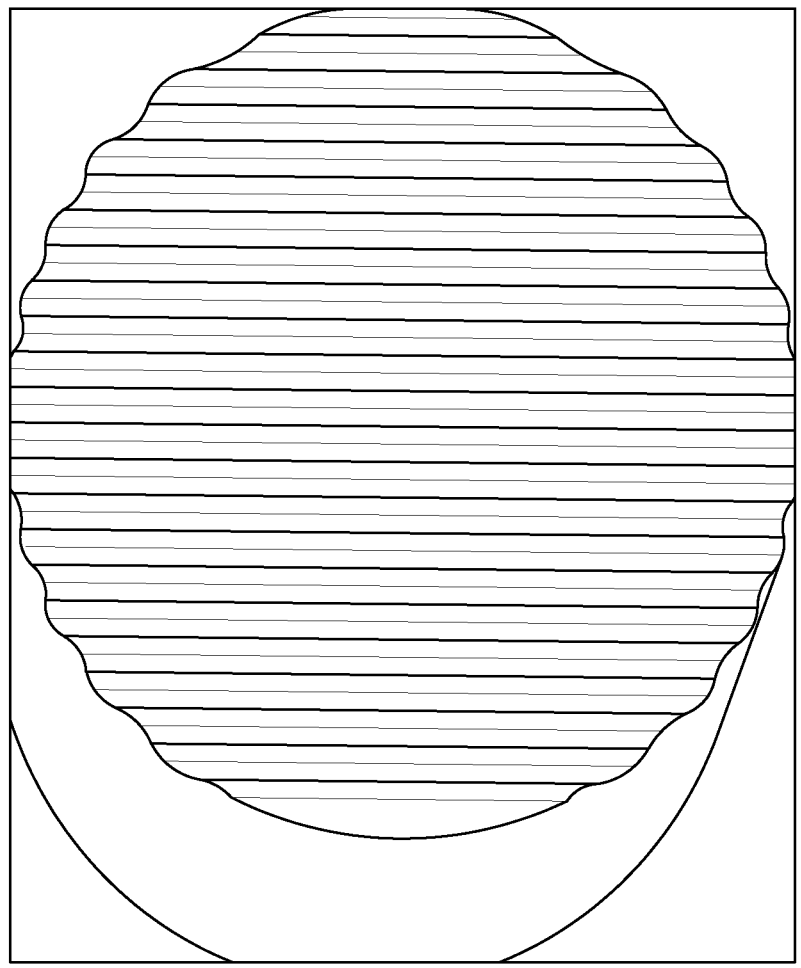
FIG. 22 shows resulted microgrooves on a flat titanium surface.

Referring to FIG. 21, schematic representations of mirror, rotary, and translation stage components to create microgrooves on femoral tray 210 are shown. Two mirrors 211 can be arranged in a specific pattern for making microgrooves at the keel surface of femoral tray 210. The present invention provides an adapter (FIG. 26) designed to grip the femoral tray 210 with the motor shaft for laser engraving on keel surface. The same mirror arrangement can be used to microgroove the flat surfaces I and II of femoral tray 210. For which, the motor can be mounted on a linear stage to provide translation of the implant to engrave entire surface of the implant (shown in view B and C). Finally, the femoral can be mounted on a combo linear and Y axis rotary stage and programmed to create microgrooves along the flat surface of III and IV (shown in view D). The above laser marking protocol was used to make microgrooves on flat surface of a titanium disc as shown in FIG. 22.

Tibia and femur bone surfaces for tibial and femoral trays are prepared using standard TKR surgical guidelines that include an extramedullary alignment guide for the tibial osteotomy and a composite cutting guide for the femoral osteotomies. Upon completion of the bone preparation, the cut surfaces of tibia and femur are flushed with saline and dried. A PCL NFM is prepared to cover the cut surface of the femoral and tibia bone. Also PCL NFM is collected on LTKR tibia keel from a parallel wire collection method (FIG. 17) or using a single disc nanofiber collectors (FIG. 18). Biomolecules immobilized PCL NFM complexes are prepared and applied to cover the cut surfaces of tibia and femur before press-fitting tibial and femoral trays in to the corresponding bone.

Figure 23:
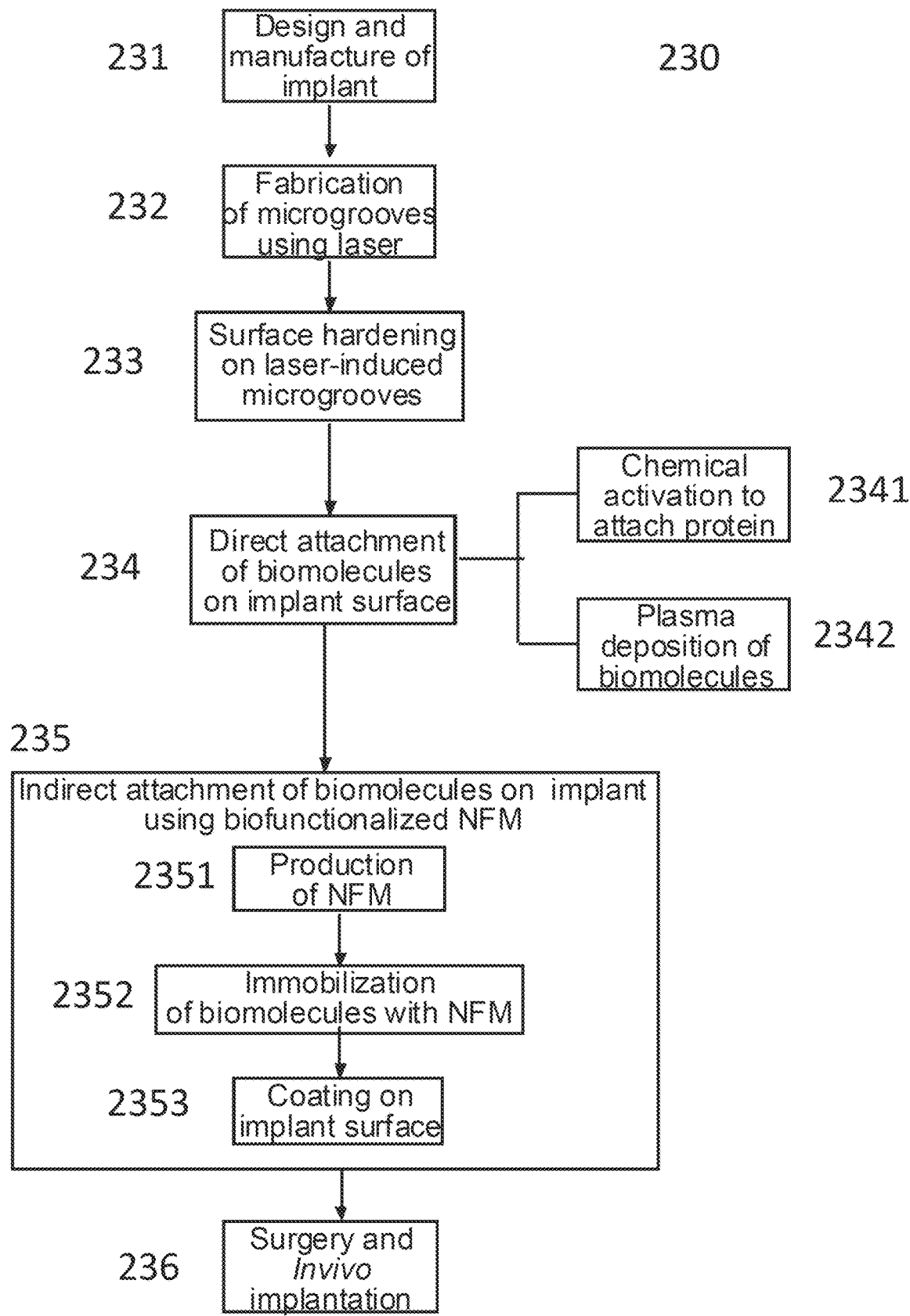
FIG. 23 shows non-limiting steps for application of biomolecules on implant surfaces using NFM.

Referring now to FIG. 23 non-limiting steps are shown for application of biomolecules on implant surface using NFM. The present invention provides a process 230 for application of NFM in cementless total hip replacement (THR) implant, as well as other types of implants and which applications are anticipated. In a preferred embodiment, titanium alloy (Ti6A14V, grade 5 [Supra alloys, Inc]) is selected as an implant because it is extensively used in orthopaedic applications and possesses a balance between strength and biocompatibility. This can use the same materials and vendors (plasma fibronectin [Thermofisher], BMP2 [GenScript], collagen [MilliporeSigma], heparin [Fisher Sci], and PCL [Sigma]) as used in our research studies, which found that these are the best materials in their respective classes for the intended purpose.

Steps:

The general steps provided by the present invention for attachment of biomolecules on implant surface using NFM is shown in FIG. 23. The following set of steps recites use of the process 230 of the present invention for attachment of biomolecules on a THR implant surface using NFM.

At 231, the invention can either use commercial available THR implant or a novel THR implant. The novel THR implant design has three major steps: (a) computational modeling of the implant that must adapt appropriate bone apposition and resorption models; (b) CNC machining from the computational model; and (c) polishing implant surface with adequate roughness.

At 232, controlled fabrication of microgrooves (>100 μm depth) on implant surfaces by laser. The rationale for laser microgrooves on implant surface is that grooves on implants protect the functional PCL NFM from applied loading and induce a higher amount of osteoblast cell function and implant-bone contact area compared to implants without grooves. Additionally, PCL NFM in grooves serve as a reservoir for the local delivery of biomolecules to increase the osseointegration of implant.

At 233, surface hardening of implant surfaces that are treated with laser (optional). Surface hardening may be necessary to remove negative surface effect resulted from laser (such as cracks, voids). Surface hardening methods such as plasma nitriding can arrest crack growth tip generated from laser.

At 234, direct attachment of biomolecules on implant surfaces may be accomplished by chemical activation or plasma deposition of biomolecules.

At 2341, chemical activation of the implant surface can provide for direct immobilization of biomolecules (e.g. hydroxyapatite, extracellular matrix proteins or cytokines or enzymes). Also chemical activation method such as tresyl chloride method can be used to covalently bond proteins on implant surface. In tresyl chloride method, basic terminal hydroxyl (OH) groups on the titanium implant surface can react with tresyl chloride (2,2,2-trifluoroethanesulfonyl chloride, $CF_3CH_2SO_2Cl$), then tresyl chloride activated Ti can directly bond with extracellular matrix proteins or cytokines (such as collagen or fibronectin).

At 2342, plasma ion deposition technique can be used to directly attached biomolecules on implant surface.

At 235, three steps are recited for indirect attachment of biomolecules on implant using biofunctionalized NFM.

At 2351, production of aligned PCL NFM using an electrospinning process as recited herein. The PCL solution may be prepared by ultrasonic mixing of 7.69 wt % of PCL pellets (pellet size~3 mm, average Mn 80,000) with acetone (laboratory reagent ≥99.5%). The solution may be poured into a glass syringe in a syringe pump for fiber production. PCL fibers can then be ejected from the glass syringe via charged needle (23G blunt needle, aluminum hub, 1 inch length, model #BX 25). The needle is charged by a high voltage power source (9 kV). Aligned fibers can be collected between two parallel wires, dual discs, or directly deposited on implant using our previously developed methods referenced herein. Collection of aligned PCL from the wire collectors along the direction of the microgrooves may be done by rotating the tresylated THR implant until the implant collects 10 μm PCL NFM of microgrooves. The reason for achieving 10 μm thickness PCL NFM is that our prior studies show reduced cell migration when PCL NFM thickness exceeds 10 μm.

At 2352, indirect attachment includes immobilization of extracellular matrix proteins with biomolecules and deposition on PCL NFM coated implant. Attachment of extracellular matrix proteins (e.g. Collagen, fibronectin) with biomolecules [such as BMP2 (Bone Morphogenetic Protein 2) or PDGF (Platelet Derived Growth Factor), nanoparticles (Ag, MgO, $TiO_2$, ZnO), enzymes, (e.g. glutathione redox components), hormones (e.g insulin)] creates complexes [such as fibronectin-BMP2 complex, fibronectin-heparin-PDGF complex].

Figure 17:
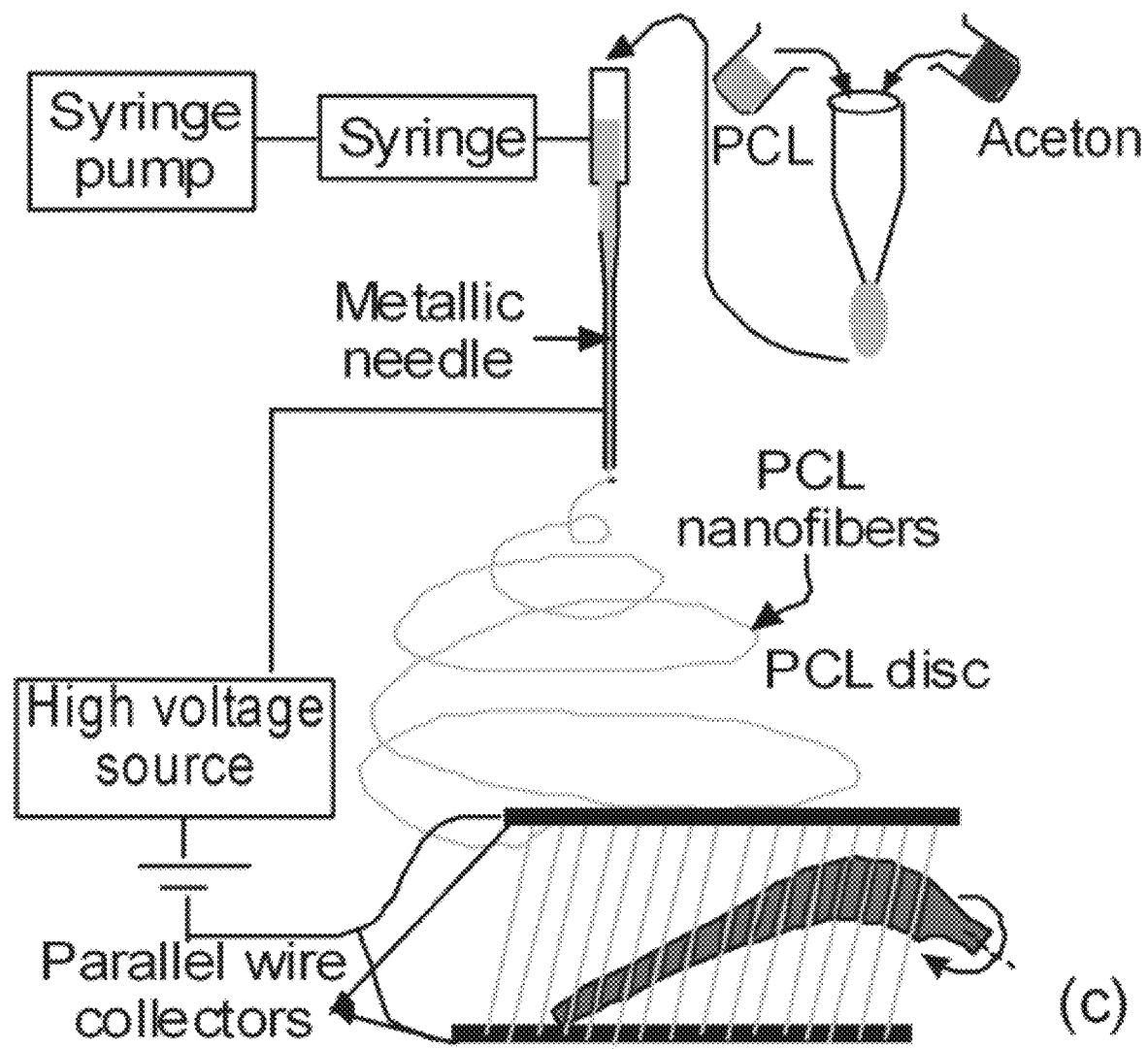
FIG. 17 shows a non-limiting schematic representation of fiber collection on a THR implant using parallel wire collection
Figure 18:
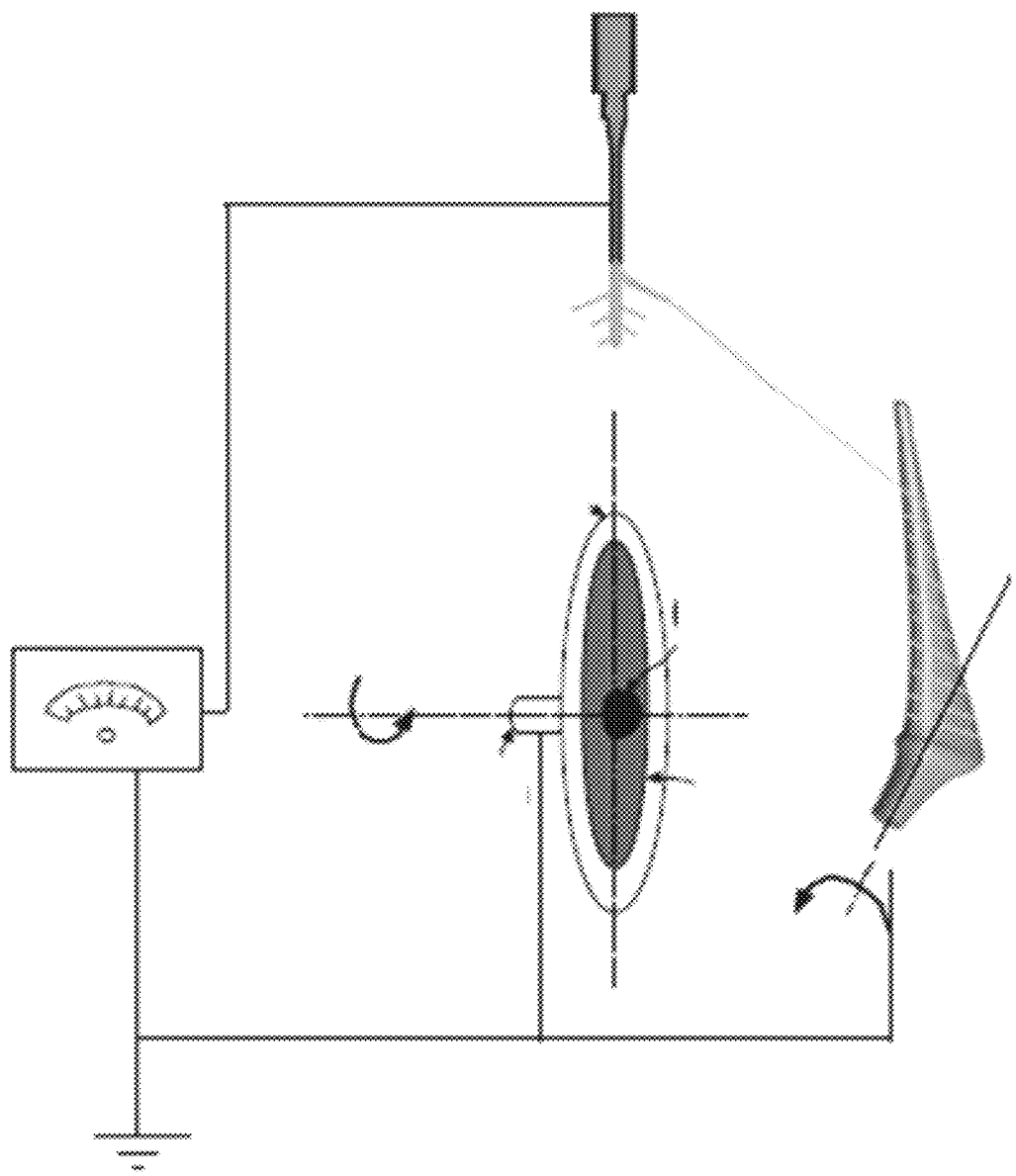
FIG. 18 shows a non-limiting schematic representation of fiber collection on a THR implant using a single disk collection method.

At 2353, coating of THR implant using the single disk fiber collection method (FIG. 18) on implant or direct coating of aligned fiber from parallel wire collector method (FIG. 17).

At 236, the fiber coated hip implant will be press-fitted in to the femur according to standard surgery protocol.

Referring again to FIG. 23 non-limiting steps are shown for attachment of biomolecules on implant surface using NFM. The present invention provides a process for application of NFM in cementless total knee replacement (TKR) implant. In a preferred embodiment the invention may use Ti-6A1-4V-eli material for TKR implant, PCL [Sigma], plasma fibronectin [Thermofisher], and human BMP2 [GenScript].

Steps:

The following set of steps recites use of the process of the present invention for attachment of biomolecules on TKR implant component surfaces (tibia and femur tray) using NFM.

At 231, the invention can either use commercial available TKR implant or a novel TKR implant. The novel TKR implant design has three major steps: (a) computational modeling of the implant that must adapt appropriate bone apposition and resorption models; (b) CNC machining from the computational model; and (c) polishing or surface finishing of implant surface with adequate roughness.

At 232, apply laser pulse to create a set of continuous microgrooves (depth=100 µm, width=100 µm, space between adjacent two grooves=100 µm) around the circumference of the keel of tibial and femur trays (FIG. 20 & FIG. 21). The reason of microgrooving is to protect functional PCL NFM at the grooves during the implantation of tibial and femur trays during TKR surgery. Apply laser pulse to create linear microgrooves on the flat surface of the tibial and femoral trays which will be joined with bone. Again this is done to increase the bone to implant surface contact area that produces a positive influence on the osseointegration of implant with bone.

At 233, surface hardening of implant surfaces that are treated with laser (optional). Surface hardening may be needed to remove negative surface effect resulted from laser (such as cracks, voids). Surface hardening methods such as plasma nitriding can arrest crack growth tip generated from laser.

At 234, direct attachment of biomolecules on implant surfaces may be accomplished by chemical activation or plasma deposition of biomolecules.

At 2341, chemical activation of the implant surface may be used for direct immobilization of biomolecules (e.g. hydroxyapatite, extracellular matrix proteins or cytokines or enzymes). Also chemical activation method such as tresyl chloride method can be used to covalently bond proteins on implant surface. In tresyl chloride method, basic terminal hydroxyl (OH) groups on the titanium implant surface can react with tresyl chloride (2,2,2-trifluoroethanesulfonyl chloride, CF3CH2SO2Cl), then tresyl chloride activated Ti can be directly bonded with extracellular matrix proteins or cytokines (such as collagen or fibronectin).

At 2342, plasma ion deposition technique can be used to directly attached biomolecules on implant surface.

At 235, three steps are recited for indirect attachment of biomolecules on implant using biofunctionalized NFM.

At 2351, production of aligned PCL NFM using an electrospinning process as recited herein. The PCL solution may be prepared by ultrasonic mixing of 7.69 wt % of PCL pellets (pellet size~3 mm, average Mn 80,000) with acetone (laboratory reagent ≥99.5%). The solution may be poured into a glass syringe in a syringe pump for fiber production. PCL fibers can then be ejected from the glass syringe via charged needle (23G blunt needle, aluminum hub, 1 inch length, model #BX 25). The needle is charged by a high voltage power source (9 kV). Aligned fibers can be collected between two parallel wires, dual discs, or directly deposited on implant using our previously developed methods referenced herein.

At 2352, indirect attachment includes immobilization of extracellular matrix proteins with biomolecules and deposition on PCL NFM coated implant. Attachment of extracellular matrix proteins (e.g. Collagen, fibronectin) with biomolecules [such as BMP2 (Bone Morphogenetic Protein 2) or PDGF (Platelet Derived Growth Factor), nanoparticles (Ag, MgO, $TiO_2$, ZnO), enzymes, (e.g. glutathione redox components), hormones (e.g insulin)] creates complexes [such as fibronectin-BMP2 complex, fibronectin-heparin-PDGF complex].

At 2353, collection of aligned PCL from the wire collectors or dual disc collectors along the direction of the microgrooves at the tibial tray keel may be conducted by rotating the tresylated implant until the keel collects 10 µm PCL NFM of microgrooves. Since the keel of femoral tray is located in a confined space, no functional NFM coating may be applied to femoral tray keel. Synthesis of extracellular matrix proteins with biomolecules and deposition on PCL NFM coated tibia keel may be conducted according to protocol discussed in step 234.

At 236, a 50 mm×50 mm dimension PCL NFM (aligned, unidirectional, 10 µm thickness) is applied to cover the cut surface of the tibia and femoral bone during the TKR surgery. To prepare the membrane, fibers may be collected between parallel wire collectors. The dual discs method referenced herein may also be used. The parallel wires or discs are placed approximately 2" distance apart to collect aligned fibers. A 50 mm×100 mm slide glass may be used to collect PCL NFM from the parallel wire collectors. Subsequently biomolecules immobilized extracellular matrix proteins are soaked by PCL NFM. Tibia and femur bone surfaces for implantation of tibial and femoral trays during TKR surgery are prepared using standard TKR surgical guidelines that include an extramedullary alignment guide for the tibial osteotomy and a composite cutting guide for the femoral osteotomies. Upon completion of the bone preparation, the cut surfaces of tibia and femur are flushed with saline and dried. Biofunctionalized NFM is applied to cover the cut surfaces of femur before the implantation of femoral tray. Each tibial tray keel is press-fitted into the tibia before depositing biomolecules immobilized PCL NFM at the interface between implant and bone.

One objective of the present invention is to improve the biological and mechanical performance of total knee replacement (TKR) surgeries using functional nanofiber coating technologies. Polymethyl methacrylate (PMMA), commonly known as bone cement, is widely used for implant fixation in total joint replacement surgeries. Implant loosening is a multi-faceted biological and mechanical process that can occur due to failure of the cement or of the bone-cement interface. The problem of aseptic loosening of cemented implant is solved by improving the biocompatibility of cement at the bone/cement interface. Our in vitro and in vivo evidence demonstrates that coating the cement with poly-ε-caprolactone nanofiber mesh (PCL NFM) improves the biocompatibility and osseointegration of cemented titanium implants. Bone morphogenetic protein-2 (BMP2) plays an important role in regulating osteoblast differentiation and subsequent bone formation. We have successfully immobilized BMP2 on PCL NFM by using plasma fibronectin (FN) in our laboratory research. FN is a glycoprotein of the extracellular matrix that also serves as a biological glue, mediating interaction between cells and extracellular matrix proteins. No published study has reported the effect of coating PMMA with BMP2-immobilized PCL NFM on the biomechanical performances of PMMA-cemented implants. The present invention provides methods for attachment of BMP2 on a PMMA-cemented implant using PCL NFM for the improvement of biological and mechanical performance of cemented implant surgeries. Immobilization of BMP2 with PCL NFM (referred as BMP2-PCL) and subsequent anchoring PMMA with bone by BMP2-PCL leads to greater in vitro and in vivo osteogenic functions in comparison to PMMA-cemented implants due to higher biological compatibility of the BMP2-PCL-coated cemented implant (referred as BMP2-PCL-PMMA).

The present invention provides a novel, independent, and supplementary approach of local delivery of a bone growth factor on a cemented implant surface using a nanofiber membrane. The advancement of in vivo implant osseointegration response after cemented implant surgery is possible from this invention. The present invention enables clinicians to use improved implanting methods for total hip or knee surgeries, thereby lowering implant loosening and preventing expensive revisions. The knowledge of immobilization and of the effect of growth factors on bone cement advances biomaterials research by providing a unique bio-functional coating that can be applied for the perfection of cemented implants and that can also be applied to other orthopedic implants, such as bone scaffolds, total hip implants, and intervertebral disc implants.

Diabetic osteopathy is characterized by microarchitectural changes that decrease bone quality leading to an increased risk of bone fracture. An ideal material for the fixation of an implant in a bone with diabetic osteopathy has not yet been achieved. Diabetics have high levels of reactive oxygen species (ROS) and not enough antioxidants to neutralize them. Diabetics also have low levels of intracellular glutathione. Enzymatic glutathione redox system components, such as glutathione (GSH), glutathione reductase (GR), glutathione peroxidase (Gpx), can neutralize excess ROS and maintain proper cellular environment, which is an important factor for the osseointegration of bone with implant. Furthermore, inflammation after a joint surgery leads to insulin resistance. Glutathione, on top of being the most potent antioxidant, is also a powerful anti-inflammatory. The nanofiber mesh with an enzymatic antioxidant can improve the osseointegration and inflammation of a TJR implant in a diabetic bone. The improvement of osseointegration and inflammation by immobilizing glutathione with the nanofiber mesh and coating the cement with glutathione-loaded nanofiber mesh was demonstrated in a rabbit diabetic bone model.

Functional Coating for Improving Osseointegration of PMMA-Cemented Implants.

Local drug delivery can attain more than a hundred times higher concentration of the drugs in surgical implant sites than can a systemic drug regimen. The immobilization of bone growth and anti-inflammatory biomolecules with bone cement via nanofiber mesh can improve bone osseointegration and control microbial-induced inflammation. Drugs can also be maintained at the implant site long enough to maintain the proper bone function around the implant without causing any side effects. In U.S. patent application Ser. No. 14/734,147 incorporated herein by reference in its entirety, and as shown in FIG. 2, we disclose a set of steps by which a NFM, composed of poly-ε-caprolactone (PCL) electrospun nanofibers, can be coated on PMMA at the interface between bone and PMMA without any detachment. The advantage of functional coating treatment on an implant is that it is simple, indirect, scalable, inexpensive, and supplementary to other surface treatment techniques. This treatment can be applied on an implant surface without affecting other implant factors, such as mechanical, medication (e.g., drugs, irradiation), and patient (e.g., age, osteopenia) factors. Clinical application of PCL NFM coating on a cemented implant provides a PCL NFM architecture to improve the osseointegration and mechanical stability of cemented implant/tissue interfaces.

Immobilization of Bone Morphogenetic Protein-2 (BMP2) with PMMA.

Bone morphogenetic proteins (BMPs) play important roles in osteoblast and chondrocyte differentiation. Among BMP family members, BMP2 is a potent osteoinductive factor that plays a key role during bone formation. Fibronectin (FN) is a multifunctional protein most abundantly found in the extracellular matrix under dynamic remodeling conditions such as bone healing and development. Research conducted by the Applicant shows that FN-immobilized PCL NFM (referred as FN-PCL) has higher biocompatibility with osteoblast cells in comparison to PCL. FN contains binding domains for many bone growth signaling factors, including BMP2 and transforming growth factor-beta (TGF-β). We have successfully immobilized BMP2 with PCL NFM, using FN in our research studies. The lasting effects of coating PMMA by BMP2-immobilized PCL NFM on the in vivo osteogenic functions of PMMA will become better known through long term use.

BMP2 has a short half-life in the blood stream, leading to a decrease in its bioactivity. Thus, a large dose of BMP2 may be required for clinical treatment. However, such a large dose of the BMP2 can cause side effects including bone overgrowth and an immune response due to diffusion away from the defected site of bone regeneration. To overcome these problems, an effective BMP2 delivery system with a sufficient time to release and appropriate concentrations must be developed for bone regeneration. The present invention provides a novel approach of nanofiber-assisted immobilization of BMP2 on a cemented metallic implant. The addition of the biologically active PCL NFM at the interface between cement and bone is a unique, indirect, and supplementary approach that will not obstruct natural bone growth on cement. PCL NFM is expected to provide for a long-term delivery of BMP2. This activation is anticipated to improve the efficacy of intraosseous implant devices by directly affecting the host's bone formation on a molecular level. This will enable clinicians to use improved implants for other total cemented joint replacement surgeries which is anticipated by the Applicant based on completed research, thereby lowering implant loosening and preventing expensive revisions. The present invention optimizes biological capabilities of the unique bio-coating for clinical implants to deliver drugs (such as osteoconductive molecules) with PMMA to adjoining bone tissue, which can increase the osseointegration and mechanical stability after TKR surgeries. The immobilization of bone growth factors (BMP2) on a human cemented implant surface via PCL NFM provides a means for the advancement of in vivo tissue-to-implant osseointegration and faster healing times of a cemented implant. Combined delivery of bone growth proteins and anti-bacterial biomolecules on cemented or cementless TKR surgeries increases osseointegration and mechanical stability and reduces inflammation of cemented implant after TJA surgeries.

In Vitro Evaluation of Coating a Cement with PCL NFM

The objective for this study was in vitro evaluation of the effect of PCL NFM coating on the osteogenic cell functions of PMMA cement using mouse osteoblast cells. Fabrication of aligned PCL fibers for coating were produced using the electrospinning process of the present invention. The fibers were collected on a glass slide as PCL discs, which were pressed on the top of PMMA during the doughy phase of PMMA. These PMMA samples were placed in an acrylic mold. The study used Cobalt$^{HV}$ bone cement (Biomet) as PMMA cement. Two groups of samples were prepared: without and with PCL-coated PMMA, referred as PMMA and PCL-PMMA, respectively. PMMA cement was prepared by mixing PMMA beads with MMA monomer at the ratio of 2:1. Our fabricated electrospun unit was used to collect aligned PCL fiber layers between the two parallel wires. A glass slide was then coated with the collected fiber. The process of fiber collection on wires and slide glass were repeated 24 times to produce PCL NFM. A 10 mm diameter PCL fiber disc was cut from the NFM using a heated punch. PMMA, while still pliable, were poured in a custom-made cell culture well. A flat-ended rod applied pressure on PMMA without and with PCL NFM discs to prepare PMMA and PCL-PMMA cements at the bottom of the well. Mouse osteoblast cells were seeded at a density of 70,000 cells/ml on cement samples and cultured for cell adhesion, proliferation, and differentiation (hydroxyapatite and osteonectin release) assays in a custom-made well using our established protocols. Significantly higher cell adhered densities were observed for PCL NFM-treated PMMA samples compared to PMMA samples ($p<0.05$). Summary statistics for the cell viability tests are shown in Table 1. Data are presented as mean±standard error. Data are presented with n=14 for both samples. Note: $p<0.05$ is denoted by * (compared to control).

TABLE 1

Parameters Descriptions

|  | PMMA | PCL-PMMA |
|---|---|---|
| Adhesion density (No. of adhered cells/image area in mm$^2$) | 232 ± 16 | 309 ± 12* |
| % of proliferation (No. of adhered cells proliferated/total no. of adhered cells × 100%) | 7.84 ± 1.28 | 9.66 ± 1.13 |
| Amount of Hydroxyapatite mineralization (area of hydroxyapatite stain/image area × 100%) | 3.06 ± 0.93 | 4.77 ± 1.02 |
| Amount of Osteonectin adsorption (area of osteonectin stain/image area × 100%) | 7.84 ± 1.28 | 9.66 ± 1.13* |

Although the cell proliferation and differentiation on the PMMA surface were higher for the PCL-PMMA samples compared to PMMA samples, the amount of cell proliferation and differentiation on each group of sample was low. The low amount of cell proliferation and differentiation of PCL NFM-coated PMMA occurred due to fact that no biomolecule was immobilized with PCL NFM to improve osteogenic properties and apatite-formation ability of PMMA. The method of the present invention coats PMMA with BMP2-immobilized PCL to create a better osteoinductive platform, with the aim of enhancing the bone growth in vivo.

Effect Coating PMMA with PCL NFM on Mechanical Stability and Osseointegration of Cemented Titanium Implant The objective this study was to evaluate the effect of PCL NFM coating on PMMA at interface between titanium (Ti) and bone on the mechanical stability and osseointegration of a PMMA-cemented implant using a rabbit model. Biomedical grade titanium (Ti-6Al-4V-eli) wire (2.2 mm diameter× 12 mm length) (Supra alloy, Inc.) was used as the implant. A total of eighteen parallel circumferential microgrooves (310 μm width, 70 μm depth, and 100 μm spacing between grooves) on Ti wire were cut by a precision diamond saw machine. The reason for making microgrooves was to avoid failure at the Ti/implant interface instead of the bone/cement interface during the mechanical tests. Our patented electrospin unit (U.S. Pat. No. 9,809,906) was used to create a cylindrical PCL NFM (length 7 mm, inside diameter 2.7 mm, and thickness 0.1 mm) by spraying PCL nanofibers on a shape collector (FIG. 17). Ti wires were anchored in rabbit femur at the epiphyso-metaphyseal junction by PMMA-only and by PMMA with cylindrical PCL NFM. Animal studies were approved by the OUHSC Institutional Animal Care and Use Committee (IACUC). Bilateral implantations were performed under anaesthetization on both legs. A 2.96 mm diameter and 6 mm deep hole was made by a hand drill in the rabbit femur. Cobalt$^{HV}$ bone cement (Biomet) was prepared by hand-mixing PMMA beads with MMA monomer using a bead:monomer ratio of 2:1. The cement was injected into the hole using a syringe. Subsequently, Ti wires was hand-pressed into the cement to prepare only PMMA-cemented Ti implant (referred as PMMA/Ti). For PCL-coated samples, the cylindrical PCL NFM was inserted into the hole. The cement was injected into the hole of the NFM using a syringe, and then Ti wires were hand-pressed into the PMMA-filled PCL to prepare the PCL-immobilized PMMA-cemented Ti implant (referred as PCL-PMMA/Ti). The animal was euthanized after 8 weeks of implantation. The bone samples having Ti were cut using a diamond saw cutter. A custom-made fixture was used to permit coaxial alignment of Ti/bone sample in the direction of pull-out force. Each Ti/bone sample was carefully fastened at the top gripper in the mechanical tester and slowly lowered to embed the sample in a low-viscosity acrylic bone cement (BioMedtrix). Pull-out tension was measure on each sample in the mechanical test stage at room temperature with a steady speed of 0.05 mm/sec. Mechanical stability was quantified by fracture strength and fatigue life. Pull-out fracture strength was calculated by dividing the force at the point of failure by the surface area of Ti in contact with bone. Pull-out cyclic tests were conducted on Ti/PMMA samples at 1 Hz with sequential 10% increments of mean load for 1000 cycles from preload (~60 N) until the failure of the bone/cement interface. Fatigue life was calculated by the total number of cycles required for the failure of the interface. Sectioning, staining, and imaging for histo-morphometric analysis of bone samples with cemented implant was done at UCO using standard histological techniques.

Our in vivo pull-out tension and cyclic tests demonstrated that PCL-PMMA/Ti has greater fracture strength (p=0.06) and fatigue life (p=0.07) compare to PMMA/Ti samples. Although these results were not statistically significantly (P>0.05), but it undoubtedly shows that PCL NFM has no negative influence on the mechanical stability. Histo-morphometric analysis confirmed that PCL NFM succeeded in holding the cement in vivo, and new bone formation occurred on both PMMA and PCL-PMMA cemented surfaces in both group of samples.

Our pilot studies showed insignificant influence of PCL NFM on fracture strength and fatigue life because the study used of a relatively high thick (~40 μm) and random fiber layers for producing the cylindrical PCL NFM. In the proposed study, we will determine the optimum architecture of PCL NFM from in vitro bone/cement studies that will significantly improve the in vivo mechanical stability of the bone/cement interface.

Immobilization of Human Bone Morphogenetic Protein-2 (BMP2) with PCL NFM Using Fibronectin (FN)

Fibronectin (FN) contains several active sites, known as the heparin-binding domains, collagen-binding domain, and cell-binding domain, that serve as platforms for cell anchorage. The PCL NFM can be modified with heparin (Hep) and further immobilized with BMP2. The modified fibers showed the potential to effectively induce osteogenic differentiation of periodontal ligament cells. Since FN contains heparin-binding domains, PCL fibers can be modified with FN-Hep-BMP2 complex. The purpose of our research was threefold: (1) to immobilize BMP2 on PCL NFM using only FN-BMP2 and FN-Hep-BMP2 complexes, (2) to determine the amount of BMP2 release from the immobilized BMP2-PCL NFM, and (3) to compare the cell viability of BMP2-immobilized PCL NFMs with PCL NFM.

We functionalized the surface of PCL NFM (produced in a way similar to that described herein) with FN-BMP2 and FN-Hep-BMP2 complexes to immobilize BMP2 with PCL NFM. We made a 10 µg/ml solution of plasma fibronectin in 1×PBS, then the solution was added to 1 ml of 10 µg/ml BMP2 and was soaked overnight at room temperature to prepare FN-BMP2 complex. Independently, 10 µg/mL of BMP2 was added to Hep (1 mg/mL), dissolved in 0.1 M MES buffer (pH 5.6), and mixed for 30 minutes to produce a Hep-BMP2 complex. The FN and Hep-BMP2 complex were mixed at a 1:1 ratio to prepare a FN-Hep-BMP2 complex. Each group of complexes was soaked with PCL NFM in a 50 ml conical tube containing 1 mL PBS (pH 7.4) and then gently shaken at 100 rpm and 37° C. for 1, 4, 7, 14, and 28 days. The supernatants were collected and replaced with fresh PBS solution at each time interval. The amount of BMP2 released was evaluated with an enzyme-linked immunosorbent assay (ELISA kit) according to the manufacturer's instructions by using a microplate reader at 450 nm. Mouse osteoblast cells (ATCC cell line #7F2) at a density of $1\times10^5$ cells/ml were seeded for 72 hours on PCL, FN-BMP2/PCL, and FN-Hep-BMP2/PCL.

In Vitro Effects of BMP2-PCL-Immobilized PMMA on Mechanical and Biological Functions Materials.

The present invention can use the chemicals (PCL [available from Sigma], plasma fibronectin [available from Thermofisher], BMP2 [available from GenScript], heparin [available from Fisher Sci] and PMMA bone Cement (available from ZimmerBiomet)] that were validated for use in our research studies.

Specimen Design and Preparation.

Our studies produced three groups of aligned bi-direction PCL NFM with different thickness (10 µm, 20 µm and 40 µm) for mechanical tests. Aligned fibers from the parallel wire were harvested at ~90° angles and stacked in layers to produce a PCL NFM on a glass slide using our patented electrospun unit. Bi-direction PCL NFM (thickness ~20 µm) were produced using the unit. To prepare the cement/bone specimen with PCL NFM at the interface, healthy canine tibia bone was harvested from a euthanized animal that was used in a separate study. Spongy bone coupon was extracted from the proximal of the tibia. The coupon was milled to bars of size (22×12×2) mm using a constant cutting speed (1000 rev/min) and feed rate (50 mm/min) to ensure consistent bone surface roughness. Each group of PCL NFM was placed on bone bar, the cement packed during the doughy phase and subsequently pressurized (60 KPa) in a custom-made mold to sandwich PCL NFM between bone and cement. Cement-PCL-Bone samples was glued with two custom holders (made using Stratasys Objet30 Pro) by high-strength metal glue. Cement-bone block (control) was prepared following exactly the same protocol without placing PCL NFM at the interface. The bone bars were maintained wet in saline during sample preparation. For cell viability tests, this study functionalized PCL NFM with 30, 60 and 120 µg/mL concentration of BMP-2 using FN and heparin following the protocol developed in an earlier study. The above concentrations were selected because these concentrations have no adverse effect on bone formation. PCL disc was produced, soaked with each concentration of FN-Hep-BMP2 complex, and pressed on PMMA in a custom-made acrylic mold for releasing, cell adhesion, proliferation, and differentiation assay using mouse osteoblast cells.

Figure 24:
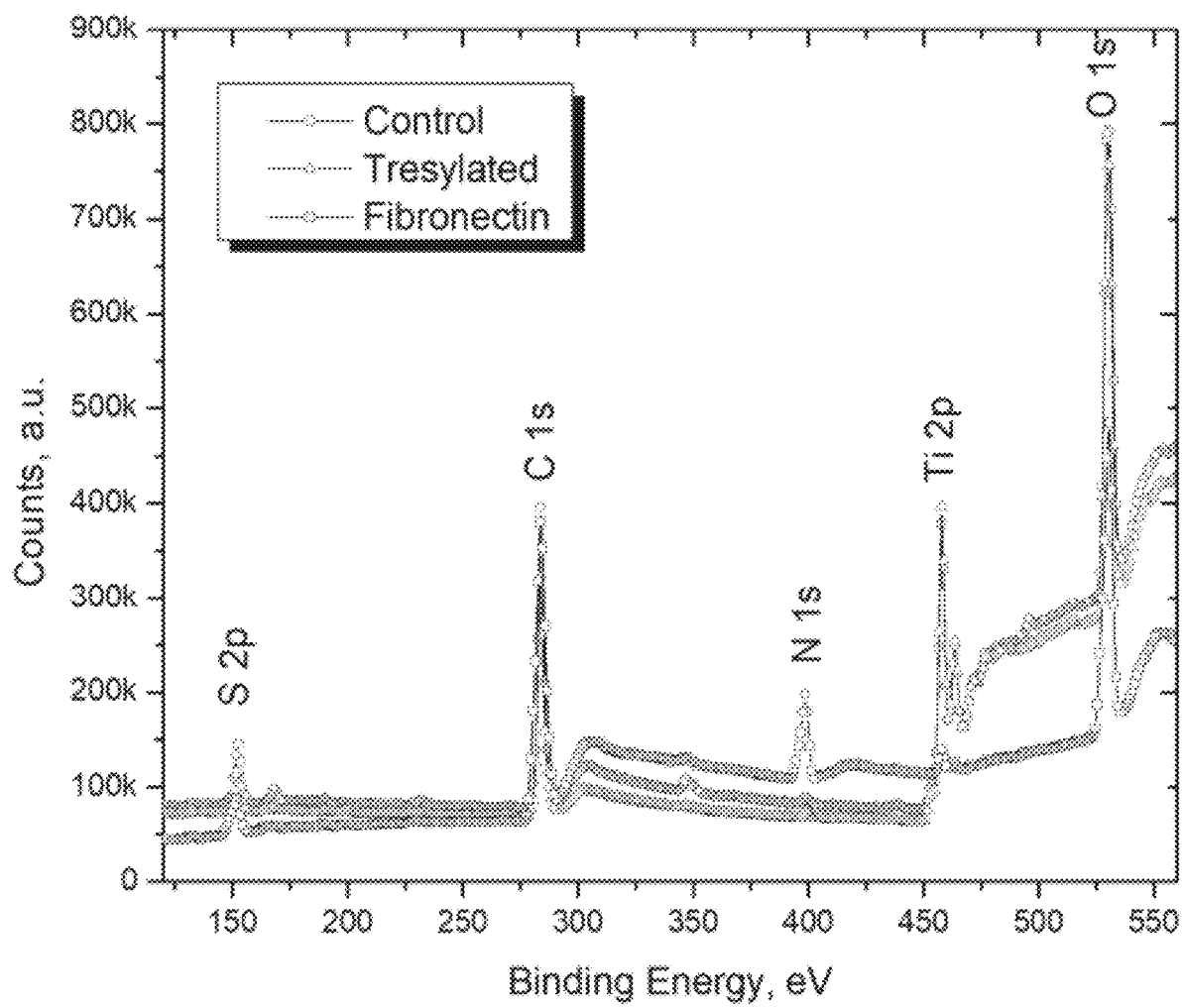
FIG. 24 shows F1s, S2p, N1s and O1s spectra of the Ti, Tresyl/Ti, and FN/Ti surface by a XPS analysis showing the direct attachment of biomolecules on titanium surface by tresla chloride method.

Immobilization of Biomolecules with Titanium:

Basic terminal hydroxyl groups of a pure titanium surface react with tresyl chloride, which allows for further coupling with biomolecules such as fibronectin (FN). Referring to FIG. 24, three groups of samples were prepared to test the FN attachment on Ti via the tresyl chloride activation process: (1) control, (2) tresyl chloride-activated Ti (referred to as Tresyl/Ti), and (3) tresyl chloride-activated Ti subsequently coupled with FN (referred to as FN/Ti). To prepare Tresyl/Ti, the top surface of a polished Ti-6Al-4V sample was treated with 2,2,2-Trifluoroethanesulfonyl chloride at 36° C. for 48 hours, then washed with water, water-acetone (50:50), and acetone. Samples were then dried and stored in a desiccator. To prepare FN/Ti, a Tresyl/Ti sample was treated for 24 hours at 37° C. with human plasma fibronectin diluted in phosphate-buffered saline (PBS) solution to a concentration of 0.1 mg/mL. X-ray photoelectron spectroscopy (XPS) analysis was conducted on all samples to determine the chemical state of Ti. As shown in FIG. 24, the binding energy for each spectrum was calibrated against the C1s peak at 284.8 eV. XPS analysis found the presence of an amide group for FN/Ti, which confirms the surface activation by tresyl chloride and then direct coupling of FN with Ti. The N1s peak, derived from the amide bond of immobilized fibronectin, was detected around the binding energy of 399.9 eV for only FN/Ti samples. Therefore, this study suggested that direct attachment of FN is possible on a tresylated Ti alloy surface.

Immobilization of Biomolecules with PCL NFM:

The rational for immobilizing these biomolecules with PCL NFM is that the resultant complexes can first be absorbed by the PCL NFM and then covalently bonded with functionally activated Ti. The rationale for attaching these biomolecules on implant is that biomolecules acts as a potent osteoinductive factor that plays a key role during bone remodeling process. Extracellular matrix proteins such as fibronectin contains several active sites, known as the heparin-binding domains, fibrin-binding domain, collagen-binding and cell-binding domain, that serve as platforms for cell anchorage. The above immobilization technique via PCL NFM is indirect, since PCL NFM will not be permanently attach to the implant and degrade with time. Also the technique is scalable, since different diameter of PCL NFM can be used for the immobilization. Finally, the technique is supplementary to other implant coating technique, since any other coating on implant can be added on laser engraved implant surface before depositing the NFM at the microgrooves.

Immobilization of Enzymatic Glutathione Redox System Using Nanofiber Mesh.

Figure 25:
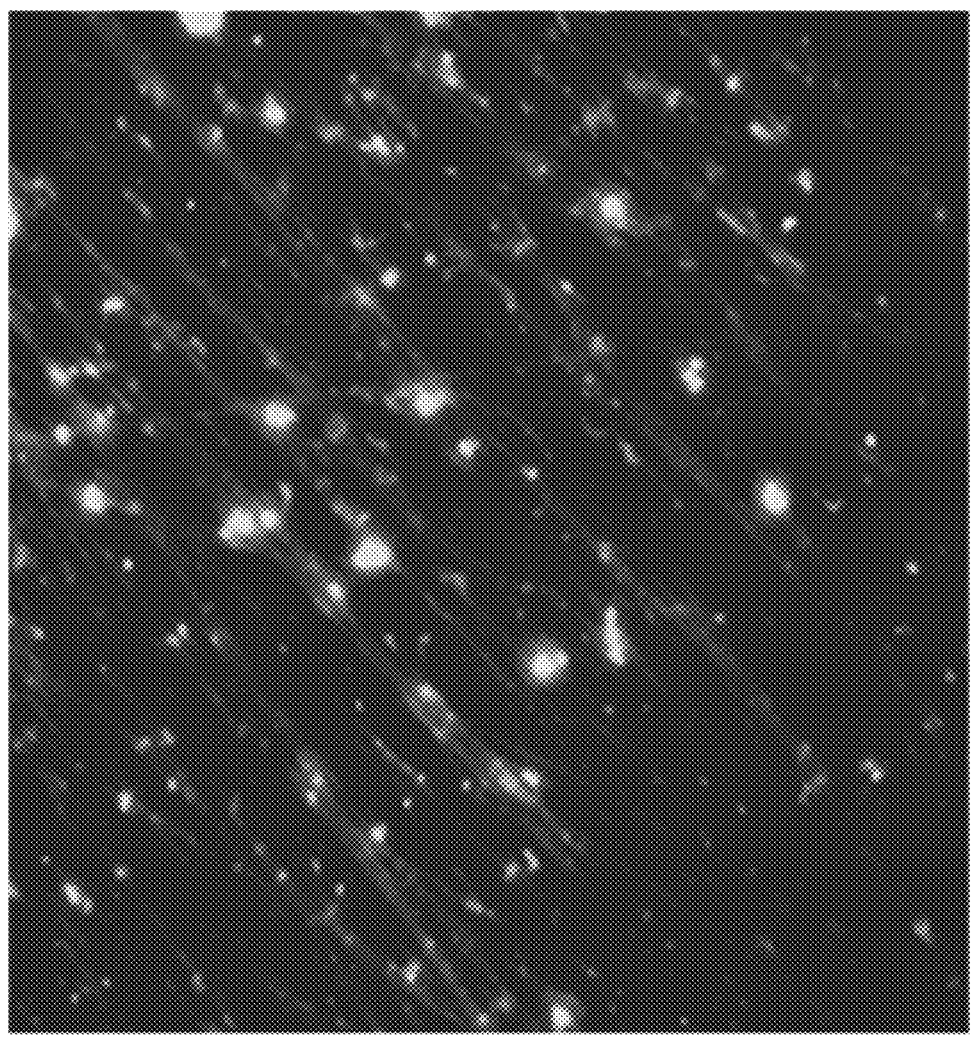
FIG. 25 shows fluorescent detection of attaching the GR on PCL NFM.

FIG. 25 shows fluorescent detection of attaching the GR on PCL NFM. Glutathione (GSH), having combined antioxidant and anti-inflammatory properties, can be immobilized with PCL NFM to maintain the bone remodeling process and confer infection resistance properties of PMMA cement in a diabetic bone. Our study results advance diabetic orthopedic research by providing an understanding of how the biocompatibility and mechanical stability of cemented implants can be improved by surface modification of cement using nanofibers loaded with drugs. Such treatment methods cannot only be applied to improve cement-to-bone interface, but can also be applied to anchor many other viscous or granular materials for tissue engineering applications. Our research provides proof of concept to deliver drugs (such as anti-microbial, osteoconductive molecules) with NFM that can further increase the osseointegration, mechanical stability, and reduction of inflammation of cemented implant after TJA. In our studies, we were able to immobilize glutathione reductase (GR) with PCL NFM after 48 hours of soaking in GR (2.5 mg/ml) with glutaraldehyde solution. The cell viability assay of aged osteoblast cells on GR-treated PCL NFM was found to be higher compared to non-GR treated cells. The application of nanofiber coating on PMMA with enzymatic glutathione redox system components may influence the bone healing process in cemented joint reconstruction.

Immobilization of Human Bone Morphogenetic Protein-2 (BMP2) with PCL NFM Using Fibronectin (FN):

Our previous studies found there was no effect of PCL-NFM coating on the Ti and PMMA surface to the apatite-formation ability, although the percentage of cell adherence and proliferation on PCL NFM-coated Ti and PMMA surfaces was significantly higher than Ti and PMMA only. We have successfully immobilized BMP2 with PCL using FN aiming to further enhance the osteogenic properties and apatite-formation ability of PCL. FN serves as a platform for cell anchorage and conjugation of PCL with BMP2. We have determined the amount of BMP2 release from BMP2-PCL and compared the apatite formation abilities of BMP2-PCL with PCL samples. We made a 10 µg/ml solution of plasma fibronectin in 1×PBS, then this solution was added to 1 ml of 10 µg/ml BMP2 and was soaked overnight at room temperature to prepare the FN-BMP2 complex. This complex was soaked with PCL NFM in a 50 ml conical tube containing 1 mL PBS (pH 7.4) and then gently shaken at 100 rpm and 37° C. for 1, 4, 7, 14, and 28 days to prepare FN-BMP2-immobilized PCL (referred simply as BMP2-PCL). The supernatants were collected and replaced with fresh PBS solution at each time interval. The amount of BMP2 released was evaluated with an enzyme-linked immunosorbent assay (ELISA kit) according to the manufacturer's instructions by using a microplate reader at 450 nm. Mouse osteoblast cells (ATCC cell line #7F2) at a density of $1 \times 10^5$ cells/ml were cultured for 72 hours on PCL and BMP2-PCL. Alkaline phosphate activity (ALP) and calcium deposition were measured for each sample group using standard protocols. The results showed BMP2-PCL released BMP2 from PCL in a sustained manner to the media for 28 days (Table 1). ALP and calcium deposition assay suggested BMP2-PCL has significantly higher apatite-formation abilities than PCL NFM only (Table 2). These results suggested that BMP2-PCL might have higher potential to induce osteogenic functions on Ti and PMMA of osteoblast cells than PCL NFM, which is not known yet. Additional study is needed to measure the effect of coating Ti and PMMA by BMP2-PCL on the osteoblast cell functions of Ti and PMMA cement and on the in vivo osteogenic functions of the Ti and PMMA cement with bone in a canine TKR model.

Immobilization of MgO Nanoparticles Using Nanofiber Mesh.

Prolonged antimicrobial and osteoinductive activities of polycaprolactone (PCL) nanofiber membrane (NFM) for biomedical application is possible by tethering the antimicrobial and osteoinductive molecules with PCL NFM. MgO NP shows promising antimicrobial properties with excellent biocompatibility with osteoblast cells in CG-PCL NFM. The effect of MgO NP tethered PCL on the antimicrobial activities of PCL-NFM was examined in our research using *Staphylococcus aureus* (*S. aureus* ATCC 6538). We have immobilized 100, 200 and 400 mg/ml of MgO nanoparticles (MgO NP) with PCL to produce three groups of MgO-PCL samples. Each of the different concentration of MgO NP was dissolved in acetone and PCL solution to prepare MgO NP-PCL solution. Aligned MgO NP immobilized PCL fibers were collected between two parallel wires using our developed electrospun machine. Eighteen layers of aligned fibers were manually collected on an acrylic mold, where two adjacent layers were oriented by 90°. The study compared the antibacterial activities against *S. aureus* of various concentration MgO NP tethered PCL NFM with an antibiotic disc (Gentamicin). The results showed that no inhibition zones for all group of MgO NP immobilized PCL samples, whereas gentamicin disc shows 5 cm inhibition zone in bacterial cultured overnight in tryptone soya agar (TSA) and Müller-Hinton agar media. However, there was no growth of the bacteria in contact with the MgO-PCL NFM at the bacterial culture plate. This results indicates that MgO NP immobilized PCL NFM inhibit bacterial growth locally. A scanning electron microscope analysis showed tethered MgO NP with PCL. A turbidity test confirmed no bacterial growth in all MgO NP immobilized PCL NFM (FIG. 10C). That led us to a conclusion that MgO NP immobilized PCL NFM coating can serve as a reservoir at PCL NFM surfaces for inhibiting infection and promoting osteoblast functions in vivo.

Fabrication of Microgrooves Using Laser:

On Curved Implant Surface:

A custom-made adapter (FIG. 26) may be used to mount the THR and TKR (tibial tray) implants in to the Z-axis rotary stage of a laser system for making microgrooves on curved surfaces. In our research, a Z-axis rotary stage was used for laser micro grooving on surface samples of cylindrical Ti. The following steps were followed to make the microgrooves on a cylindrical Ti surface:

Draw the architecture of microgrooving pattern using autoCAD software and convert the file to vector (DXF) file.

Open the vector file using the laser marking software "Marker.exe"

Make sure the vertical length to shoot the laser is 244 mm.

Insert the Ti rod in the rotary motor vice. Fix it tightly between the jaws.

Using the LIGHT command, make sure the trace of the lines are within permissible limits.

Figure 27:
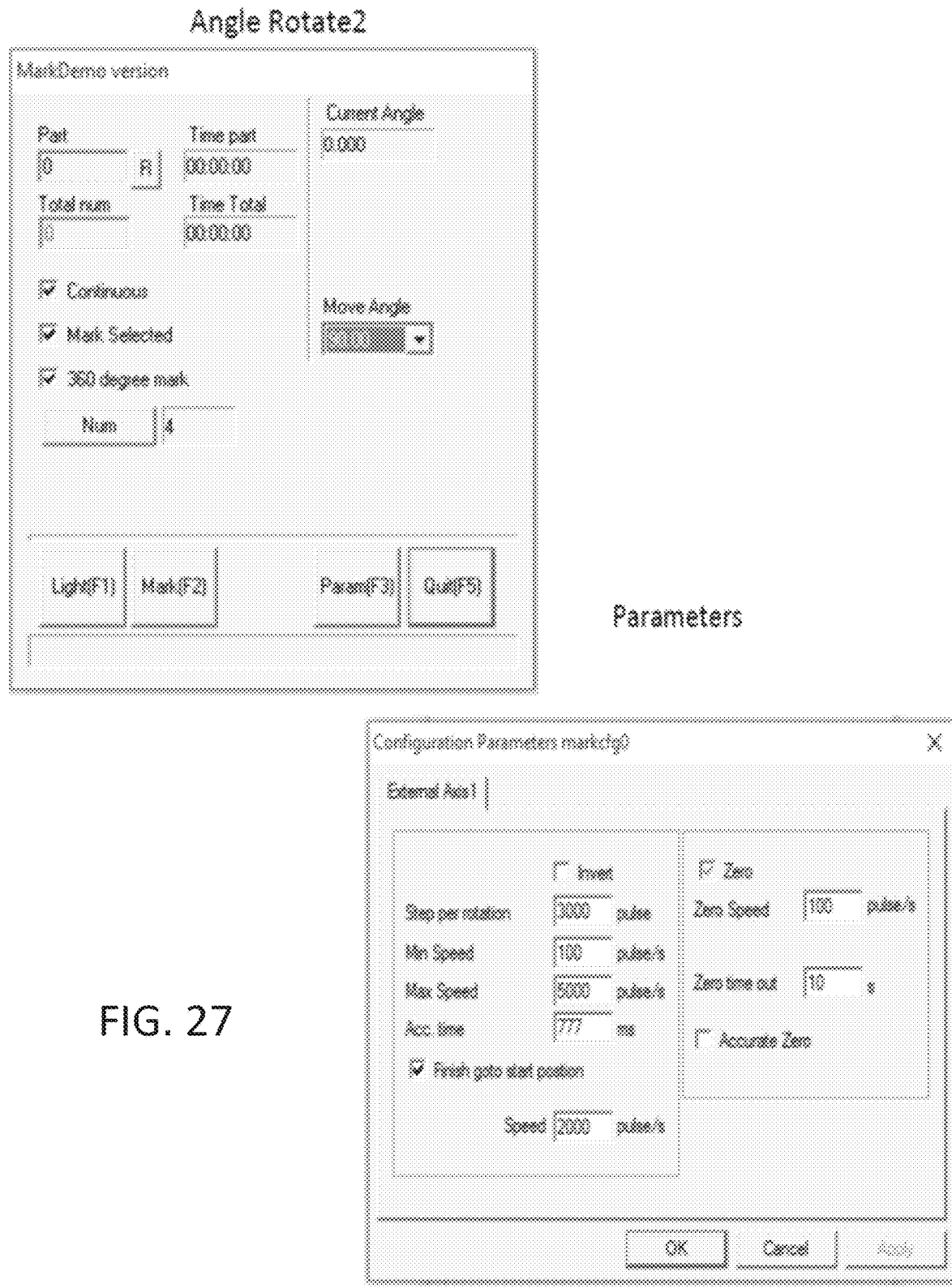
FIG. 27 shows a non-limiting parametric settings for laser cutting THR and TKR (tibial tray) implants in a Z-axis rotary stage of a laser system.

Open Laser>Angle rotate 2 and set the parameters as shown in FIG. 27.

Press MARK. Make sure the rotary motor is rotating while grooving. Observe the rotary motor for every 7 parts to ensure the motor is rotating.

Usually it takes 40 minutes for 1 sample and the part number goes to 37-40.

After grooving both the samples, polish them to remove away the debris by polishing it very gently using the 9 µm fluid and polishing paper for about 2 minutes.

For THR implant, a set of continuous microgrooves (depth=100 µm, width=100 µm, space between adjacent two grooves=100 µm) around the circumference of THR are engraved using a fiber-marking laser system. The microgrooves need to be oriented proximally by 60° from the normal direction of the stem surface because such groove orientation generates maximum stress distribution from implant to the adjacent bone. A custom-made base capable of orienting X-Y plane any angle was used to create microgrooves around the circumference of the implant at 60° angle. The above I-IX protocols can be followed to make the microgrooves on a THR implant. A custom made adapter may be used to install a TKR or THR implant component in a stepper motor gripper.

For TKR implant, a similar set of continuous microgrooves (depth=100 µm, width=100 µm, space between adjacent two grooves=100 µm) around the circumference of the tibial tray keel can be engraved using a fiber-marking laser system. A custom made adapter may need to be designed to grip the tibial tray with the motor shaft for laser engraving on keel surface (FIG. 20A). FIG. 20B shows the schematic view of laser grooving after making the microgrooves.

A pair of mirrors can be arranged in a specific pattern for making microgrooves at the keel surface of femoral tray (FIG. 21A). A custom made adapter may need to be designed to grip the femoral tray with the motor shaft along the axis of rotation for laser engraving on keel surface.

On Flat Implant Surface:

The above same mirror arrangement shown in FIG. 21 can be used to microgroove the flat surfaces I and II of femoral tray. For which, the motor can be mounted on a linear stage to provide translation of the implant to engrave entire surface of implant (FIGS. 21B and 21C. Finally, the femoral can be mounted on a combo linear and Y axis rotary stage and programmed to create microgrooves along the flat surface of III and IV (FIG. 21D). The above laser marking protocol was used to make microgrooves on flat surface of a titanium disc as shown in FIG. 22.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

We claim:

1. A process to functionalize nanofiber membrane (NFM) on a total joint replacement (TJR) implant surface to support bone ingrowth and reduce macrophage-associated inflammation, comprising;
    amending said implant surface by laser cutting microgrooves greater than 100 µm in depth to protect Polycaprolactone (PCL) nanofiber membrane (NFM) from applied loading, induce a higher amount of osteoblast cell function, increase implant-bone contact area, and serve as a reservoir for the local delivery of biomolecules to increase the osseointegration of said implant;
    depositing aligned fibers on said implant surface, said fibers aligned in the direction of the microgrooves and collected in layers until a thickness is reached preferably in the range of 1 µm to 10 µm,
    wherein, biofunctionalized nanofiber membrane (NFM) are used to indirectly attach biomolecules on said implant surface.

2. The process of claim 1, further comprising chemically activating said implant surface to produce direct immobilization of biomolecules.

3. The process of claim 2, wherein said biomolecules include any of hydroxyapatite, extracellular matrix proteins or cytokines, or enzymes.

4. The process of claim 2, wherein chemical activation covalently bonds proteins on said implant surface.

5. The process of claim 1, further comprising using a plasma ion deposition technique to directly attach biomolecules on said implant surface.

6. A total joint replacement (TJR) implant including nanofiber membrane (NFM) functionalized to support bone ingrowth and reduce macrophage-associated inflammation, said implant functionalized using the process of claim 1.

7. The total joint replacement (TJR) implant of claim 6, wherein said implant surface is chemically activated to produce direct immobilization of biomolecules.

8. The total joint replacement (TJR) implant of claim 7, wherein said biomolecules include any of hydroxyapatite, extracellular matrix proteins or cytokines, or enzymes).

9. The total joint replacement (TJR) implant of claim 7, wherein proteins are covalently bonded on said implant surface.

10. The total joint replacement (TJR) implant of claim 7, wherein biomolecules are directly attached on said implant surface using a plasma ion deposition technique.

11. A process to functionalize nanofiber membrane (NFM) on a total joint replacement (TJR) implant surface to support bone ingrowth and reduce macrophage-associated inflammation, comprising:
    amending said implant surface by laser cutting microgrooves greater than 100 µm in depth to protect Polycaprolactone (PCL) nanofiber membrane (NFM) from applied loading, induce a higher amount of osteoblast cell function, increase implant-bone contact area, and serve as a reservoir for the local delivery of biomolecules to increase the osseointegration of said implant;
    depositing aligned fibers on said implant surface, said fibers aligned in the direction of the microgrooves and collected in layers until a thickness is reached preferably in the range of 1 µm to 10 µm,
    wherein, extracellular matrix proteins with biomolecules are immobilized and deposited on said Polycaprolactone (PCL) nanofiber membrane (NFM) coated implant.

12. The process of claim 11, further comprising attachment of extracellular matrix proteins including either Collagen or fibronectin, with biomolecules including either Bone Morphogenetic Protein 2 (BMP2) or Platelet Derived Growth Factor (PDGF).

13. The process of claim 11, further comprising addition of nanoparticles, enzymes, hormones or protein complexes.

14. The process of claim 13, wherein nanoparticles include any of silver (Ag), magnesium oxide (MgO), titanium dioxide ($TiO_2$), Zinc oxide (ZnO).

15. The process of claim 13, wherein enzymes include glutathione redox components.

16. The process of claim 13, wherein hormones include insulin.

17. The process of claim 13, wherein protein complexes include fibronectin-BMP2 complex or fibronectin-heparin-PDGF complex.

18. A total joint replacement (TJR) implant including nanofiber membrane (NFM) functionalized to support bone ingrowth and reduce macrophage-associated inflammation, said implant functionalized using the process of claim 11.

19. The total joint replacement (TJR) implant of claim 18, further comprising extracellular matrix proteins including either Collagen or fibronectin, with biomolecules including either Bone Morphogenetic Protein 2 (BMP2) or Platelet Derived Growth Factor (PDGF).

20. The total joint replacement (TJR) implant of claim 18, further comprising any of nanoparticles, enzymes, hormones or protein complexes, wherein nanoparticles include any of silver (Ag), magnesium oxide (MgO), titanium dioxide ($TiO_2$), Zinc oxide (ZnO), enzymes include glutathione redox components, hormones include insulin, and protein complexes include fibronectin-BMP2 complex or fibronectin-heparin-PDGF complex.

* * * * *

UNITED STATES PATENT AND TRADEMARK OFFICE
CERTIFICATE OF CORRECTION

| | |
|---|---|
| PATENT NO. | : 10,932,910 B2 |
| APPLICATION NO. | : 16/248122 |
| DATED | : March 2, 2021 |
| INVENTOR(S) | : Morshed Khandaker, Shahram Riahinezhad and William Paul Snow |

Page 1 of 1

It is certified that error appears in the above-identified patent and that said Letters Patent is hereby corrected as shown below:

In the Specification

At Column 1, please delete Lines 57-60 and insert in its place the following:
--This invention was made with government support under GM103447 awarded by the National Institutes of Health. The government has certain rights in the invention.--

Signed and Sealed this
Eighth Day of November, 2022

Katherine Kelly Vidal
*Director of the United States Patent and Trademark Office*